United States Patent [19]

Pursley et al.

[11] Patent Number: 5,180,380

[45] Date of Patent: * Jan. 19, 1993

[54] AUTOMATIC COMPRESSION-DISTRACTION-TORSION METHOD AND APPARATUS

[75] Inventors: John A. Pursley; Jordan M. Holloway, both of Indian; Thomas L. Wakefield, Anchorage, all of Ak.

[73] Assignee: Autogenesis Corporation, Anchorage, Ak.

[ * ] Notice: The portion of the term of this patent subsequent to Nov. 27, 2007 has been disclaimed.

[21] Appl. No.: 548,814

[22] Filed: Jul. 6, 1990

Related U.S. Application Data

[63] Continuation of Ser. No. 320,586, Mar. 8, 1989, Pat. No. 4,973,331.

[51] Int. Cl.$^5$ .............................. A61B 17/56
[52] U.S. Cl. ...................... 606/54; 606/56; 606/58; 606/59
[58] Field of Search .............. 606/53, 54, 55, 56, 606/57, 58, 59

[56] References Cited

U.S. PATENT DOCUMENTS

| | | | |
|---|---|---|---|
| 3,941,123 | 3/1976 | Volkov | 606/55 |
| 3,976,060 | 8/1976 | Hildebrandt | 606/58 |
| 3,977,397 | 8/1976 | Kalnberz | 606/56 |
| 3,985,127 | 10/1976 | Volkov | 606/55 |

(List continued on next page.)

FOREIGN PATENT DOCUMENTS

| | | |
|---|---|---|
| 2417233 | 10/1975 | Fed. Rep. of Germany . |
| 2705154 | 2/1977 | Fed. Rep. of Germany . |
| 2601938 | 7/1977 | Fed. Rep. of Germany . |
| 2845647 | 5/1980 | Fed. Rep. of Germany . |
| 3722595 | 1/1989 | Fed. Rep. of Germany . |
| WO89/11255 | 11/1989 | World Int. Prop. O. . |

OTHER PUBLICATIONS

Soviet Inventions, Illustrated, week 8519, Jun. 19, 1985, section P/Q, class P31, abstract No. 85 115442/19, Derwent Publications Ltd., London, Great Britain, and SU 1122308, Kurgan Orthopaedics, 1984.

"Operative Lengthening of the Femur Using a Completely Implantable Distractor Apparatus" by A. N. Witt and M. Jager, Arch. of Orthop, and Traumat. Surg. 92, 291–296 (1978), (English translation provided).

"Results of Animal Experiments with a Fully Implantable Distractor Apparatus for Operative Leg Lengthening" by A. N. Witt, M. Jager, H. Bruns, W. Kusswetter, J. J. Hildebrandt, R. Cramer and A. Vogel, Arch. of Orthop. and Traumat., Surg. 88, 273–279 (1977) (English translation provided).

"Development of a Fully Implantable Distractor-Device for Operative Leg-Lengthening", 6th International Symposium on External Control of Human Extremeties in Dubrovnik, Yugoslavia Hildebrandt, J. J., Cramer, R. Jager, M. Vogel, A. (1978).

Vollinplantierbaren Distraktiions-gerat fur die operative Beinverlangerung, Teil I: Konstruktion und Anwendung im Tierversuch, J. J. Hildebrandt, R. Cramer, (List continued on next page.)

*Primary Examiner*—Michael A. Brown
*Attorney, Agent, or Firm*—Dickstein, Shapiro & Morin

[57] ABSTRACT

An orthopaedic system is provided which includes a plurality of support members, a plurality of rods interconnecting the support members, a plurality of pins attached to the support members for passing through bone of a patient, and an automatic drive device to control an adjustment mechanism of the rods to adjust the rod length of the rods to alter the relative positions of the support members. The drive device includes at least one motor for incrementally adjusting the adjustment mechanism of at least one of the rods and a controller device for providing pulses to the motor and for storing information regarding the number of stepwise adjustments of the rod length by the motor.

32 Claims, 23 Drawing Sheets

U.S. PATENT DOCUMENTS

| | | | |
|---|---|---|---|
| 4,033,340 | 7/1977 | Kalnberz | 606/56 |
| 4,338,927 | 7/1982 | Volkov | 606/56 |
| 4,570,625 | 2/1986 | Harris et al. | 606/58 |
| 4,615,338 | 10/1986 | Ilizarov | 606/58 |
| 4,768,524 | 9/1986 | Hardy | 606/54 |
| 4,784,125 | 11/1988 | Monticelli | 606/56 |
| 4,923,458 | 4/1990 | Fischer | 606/59 |
| 4,973,331 | 11/1990 | Pursley | 606/54 |

OTHER PUBLICATIONS

A. Vogel, M. Jager, H. Bruns, H. Stritzinger, Fachtagungen Medex, Basel/Schweiz (1976), Biomed. Techn., Band 21, 259–260, Erganzunsband Jun. 1976.

Operative Beinverlangerungmiteinem Vollinplantierbaren Distraktionsgerat by J. J. Hildebrandt, M. Jager and A. N. Witt.

"Continuous Femur Lengthening with Intramedullary Stabilization", J. Gotz and W. D. Schellman, Arch. of Orthop. and Traumat. Surg. 82, 305–310 (1975), (English translation provided).

"The Extension Pin, A New Way of Lengthening the Femur and Tibia" by F. Baumann and J. Harms, Arch. of Orthop and Traumat. Surg. 90, 139–146 (1977), (English translation provided).

AUTOMATIC COMPRESSION-DISTRACTION-TORSION METHOD AND APPARATUS

This application is a continuation of application Ser. No. 07/320,586, filed Mar. 8, 1989, now U.S. Pat. No. 4,973,331.

FIELD OF THE INVENTION

The present invention is directed to medical equipment used in orthopaedics and traumatology to treat various congenital and acquired shortenings and other defects or skeletal seqments, and, more particularly, the invention is directed to a drive system for a compression-distraction-torsion apparatus.

BACKGROUND OF THE INVENTION

U.S. Pat. No. 4,615,338 (incorporated by reference herein) to Ilizarov discloses an orthopaedic procedure employing an external device which fixes to the bone by means of slender pins and which tensions or distracts the bone at a doctor-selected rate and rhythm of tensioning or distraction, with resulting growth of new bone, skin, muscle and nerves. The Ilizarov external fixation system uses a variety of perforated rings connected by graduated telescopic rods. Generally, the rods are distracted ¼ of a millimeter four times a day for a total distraction of 1 mm per day. When the desired length is achieved, the bone is then held in place to allow consolidation. The consolidation period is generally the same as the time needed for distraction, generally. Thus, for a distraction period of four weeks, the consolidation period would be four weeks, for a total treatment time of eight weeks. Research shows that a rate of distraction of 1/60 of a mm sixty times a day produces even better results than ¼ of a mm increments.

Generally, in the Ilizarov system, the nuts of the graduated telescopic rods interconnecting the support members are turned manually to cause distraction. U.S. Pat. No. 4,615,338 discloses an automatic drive system employing a lead screw mated with a ratchet wheel placed in a housing, and a pawl interacting with teeth of the ratchet wheel to drive the ratchet wheel to adjust the length of the telescopic rod.

SUMMARY OF THE INVENTION

It is an object of the present invention to provide an autodistractor system which employs at least one motor to adjust the length of a rod member in an Ilizarov-type system, and a programmable controller which controls the motor or motors and stores information regarding the rod length adjustments.

It is a further object of the present invention to provide a compression-distraction-torsion apparatus employing a programmable controller whereby a doctor can adapt the system to particular needs based on the number of motors, the process type (i.e., compression, distraction or torsion), the number of millimeters advancement per day, the number of times the motor or motors are to be advanced per day to achieve the desired total daily advancement, and the total movement required for the overall treatment.

The above and further objects of the present invention are achieved in a surgical, orthopaedic apparatus which comprises a plurality of support members; a plurality of rods interconnecting the support members, the rods including adjustment means for enabling the rod length to be adjusted; a plurality of pins attached to the support members, the pins including means for passing through bone of a patient; and an automatic drive means for controlling the adjustment means of the rods to adjust the rod length of the rods to alter the relative positions of the support members. The drive means comprises at least one motor (which may be a digital motor) for incrementally adjusting the adjustment means to stepwise adjust the rod length, and a controller means for providing pulses to the motor to control the incremental adjustments of the rod length and for storing information regarding the number of stepwise adjustments of the rod length by the motor during an overall treatment procedure. The invention typically includes a plurality of motors corresponding in number to the plurality of rod members.

The invention can further include a feedback sensor means for sensing the amount of adjustment of the length of the rods and for providing data representing the sensed amount of adjustment to the controller means. The controller means can further include a comparator means for comparing the information regarding the number of stepwise adjustments with the data representing the sensed amount of adjustment.

The apparatus can further include a manual control means for controlling the adjustment means of the rods to adjust the rod length in order to alter the relative positions of the support members, and a switch means for selecting between a manual mode in which only the manual control means controls the adjustment means of the rods and an automatic mode in which only the automatic drive means controls the adjustment means.

The support members can comprise a ring having a plurality of radially extending through holes having said pins extending therethrough. The rods can comprise a graduated telescopic rod, and the adjustment means of the rods can comprise a nut. The motors can be mounted on the graduated telescopic rods.

The apparatus can include a gear mount ring mounted around the nut of the telescopic rods, with the gear mount ring comprising, on one end, a detent latching loop engaged with a projection of the nut such that the gear mount ring and the nut are rotatable in concert with one another and, on its other end, an internal gear ring. A gear box is connected to the motor and includes an output gear comprising a gear means for engagement with the internal gear ring of the gear mount ring. The apparatus can further include means for enabling the gear mount ring to move axially relative to the nut so as to cause the gear mount ring to disengage from the output gear while maintaining engagement between the detent latching loop and the projection of the nut. As a result, when the gear mount ring is disengaged from the output gear, a manual mode is provided in which the nut can be manually rotated, and when the gear mount ring is engaged with the output gear, an automatic mode is provided in which the nut can be rotated by the automatic drive means.

The feedback sensor means can be an infrared sensor or a magnetic reed switch.

The apparatus can further include a display means, connected to the controller means, for displaying a representation of the information regarding the number of stepwise adjustments of the rod length during the overall treatment procedure.

According to the invention there is also provided a method of controlling a surgical, orthopaedic apparatus which includes a plurality of support members; a plurality of rods interconnecting the support members, the rods including adjustment means for enabling the rod length to be adjusted; and a plurality of pins attached to the support members, the pins including means for passing through bone of a patient. The method comprises controlling the adjustment means of the rods to adjust the rod length to adjust the relative positions of the support members by employing a plurality of motors corresponding to the plurality of rods to incrementally adjust the adjustment means to stepwise adjust the rod length and employing a controller means to provide pulses to the motors to control the incremental adjustments of the rods and to store information regarding the number of stepwise adjustments of the rod length by the motors.

The method can further comprise sensing the amount of adjustment of the rod length and providing data representing the sensed amount of adjustment to the controller means based on a comparison of the information regarding the number of stepwise adjustments with the data representing the sensed amount of adjustment. The method can further comprise displaying a representation of the information regarding the number of stepwise adjustments of the rod length.

The method can further comprise providing a test pulse to each one of the motors and checking whether each of the motors responds properly to the pulse. The method can further comprise (i) storing in a counter a predetermined count representing a total number of pulses required to be sent to each motor to step the motor a required amount at each advance cycle and a total cycle count representing a number of advance cycles required for each of the motors to achieve a desired total treatment movement; (ii) providing a control pulse to a first one of the motors to advance it one increment; (iii) determining whether the first one of the motors is turned on in response to the control pulse; (iv) turning off the first one of the motors; (v) determining whether the first one of the motors is turned off; (vi) decrementing the predetermined count stored in step (i) to provide a decremented count responsive to the first one of the motors being advanced one increment; and (vii) checking whether the decremented count obtained in step (vi) is greater than zero, and if so, repeating steps (ii)-(vi) with respect to the first one of said digital motors. The method can further comprise, responsive to a determination that the decremented count obtained in step (vi) is equal to zero, storing again in the counter the predetermined count and performing steps (i)-(vii) successively with respect to all other ones of the motors to complete an advance cycle for the motors.

The method can further comprise counting a number of the advance cycles carried out with respect to the motors; comparing the number of advance cycles with the total cycle count representing the number of advance cycles required to achieve the desired total treatment movement; performing steps (i)-(vii) with respect to the motors to carry out another advance cycle after a predetermined time delay responsive to a determination that the number of advance cycles is less than the total cycle count; and terminating the treatment responsive to a determination that the number of advance cycles is equal to the total cycle count.

The above and other objects, advantages and features of the invention will be more fully understood when considered in conjunction with the following discussion and to the attached drawings.

DETAILED DESCRIPTION OF THE PREFERRED EMBODIMENTS

Figure 1B:
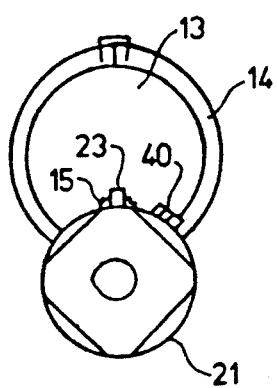
FIGS. 1A-1D illustrate the autodistractor/compressor motor assembly according to the invention mounted on a telescopic rod.
Figure 1A:
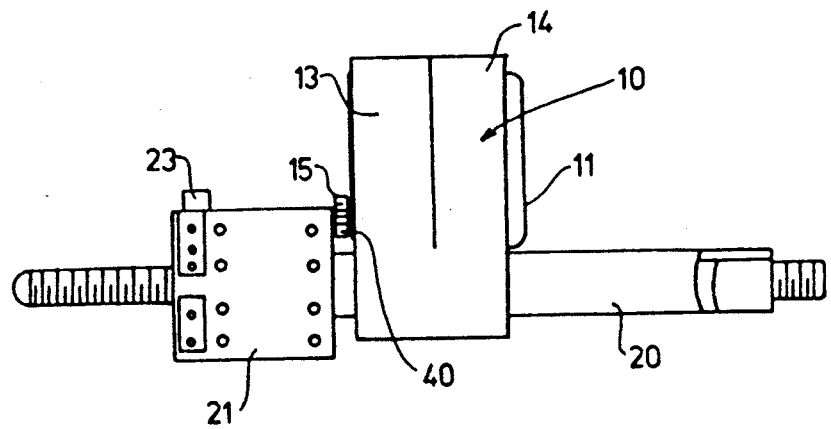
Figure 1D:
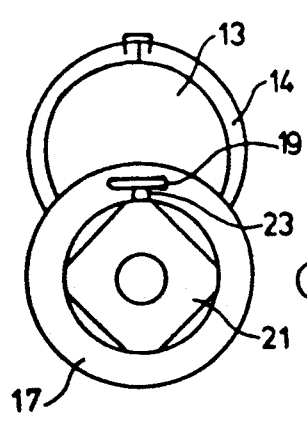
Figure 1C:
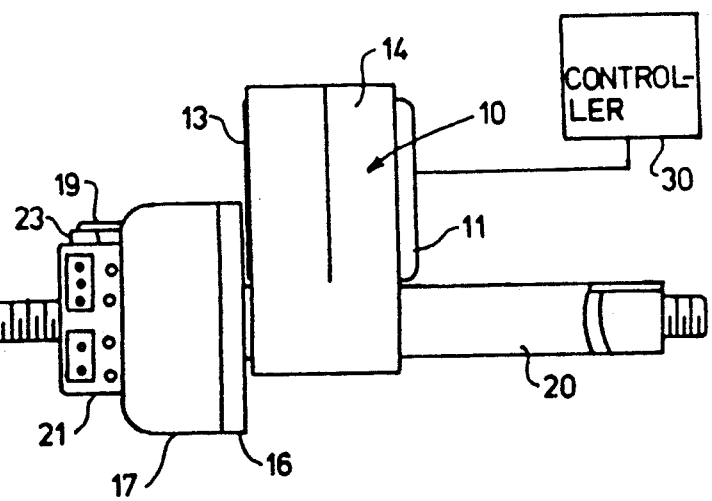

FIGS. 1A-1D show the autodistractor/compressor/torsioner motor assembly 10 according to the invention mounted on a telescopic rod 20. The assembly includes a motor 11 (which may be a digital motor) mounted via motor mount 14 onto rod 20, gear box 13 associated with motor 11, and an output gear 15 controlled by motor 11. A gear mount ring 17 is mounted on nut 21 of graduated telescopic rod 20. Gear mount ring 17 includes a detent latching loop 19 which engages with a projecting member 23 of nut 21 and an internal gear ring 16 which engages with output gear 15 of the digital motor-gear box combination. Member 23 is a spring loaded detent latch which locks at 90° rotations of nut 21. Detent latching loop 19 holds the latch open to allow rotation of nut 21 by the motor means. When gear mount ring 17 is in the manual mode, latch 23 performs normally. Set screw 18 (FIG. 2) passes through a through bore in gear mount ring 17 and abuts against nut 21. In this manner, motor 11 controls rotation of gear mount ring 17 and, in turn, nut 21. Gear mount ring 17 can be manually moved in the direction of arrow A so as to provide a switching means to select between a manual mode in which internal gear ring 16 is disengaged from output gear 15 so that nut 21 can be rotated manually and an automatic mode in which internal gear ring 17 is coupled with output gear 15 such that motor 11 is able to rotate nut 21.

A programmable controller (CPU 30), which is programmable in a manner discussed below is connected to motor 11 to provide signals thereto to control the stepwise or incremental adjustments of nut 21 and, hence, of the length of rod 20. As described in detail below, controller 30 also stores information regarding the number of stepwise adjustments of the rod length by motor 11 during the overall treatment procedure. This information is converted into a format readily comprehensible by a doctor and displayed on a display 140 (see FIG. 7) to enable determination of the progress of the overall treatment.

A feedback sensor 40 is provided to sense the actual amount of physical adjustment of the length of rod 20. Sensor 40 is preferably an infrared sensor, but may also be a magnetic reed sensor. In the magnetic sensor embodiment, a magnet is mounted on e.g., gear 15, ring 17 or nut 21; when the magnet lines up with the magnetic reed switch, a signal is sent back to controller 30. The magnetic sensor embodiment, however, is not preferred due to its sensitivity to the presence of external electromagnetic fields. In the infrared embodiment, sensor 40 receives infrared light reflected off a reflector 40A (FIG. 8) mounted, e.g., on gear mount ring 17. Reflector 40A could also be mounted, e.g., on nut 21 or gear 15. Specifically, sensor 40 enables controller 30 to count and store the number of revolutions of gear mount ring 17 and hence nut 21. Sensor 40 thus provides data to controller 30 representing the sensed amount of adjustment of the rod length. Controller 30 includes a means for comparing this sensed adjustment amount with the stored information regarding the number of stepwise adjustments of the rod length. If a non-equivalence is detected, an investigation of its cause will be carried out.

Figure 2:
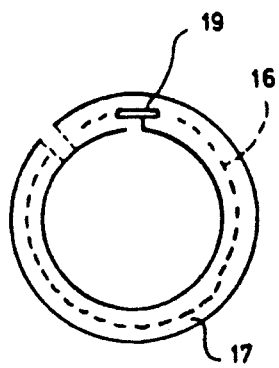
FIG. 2 is a top view of a gear mount ring of the FIG. 1 system.
Figure 3:
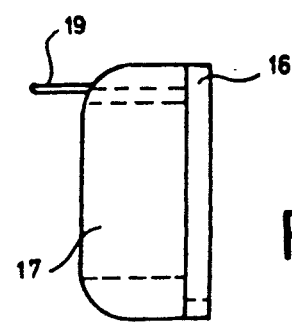
FIG. 3 is a side view of the gear mount ring.
Figure 4:
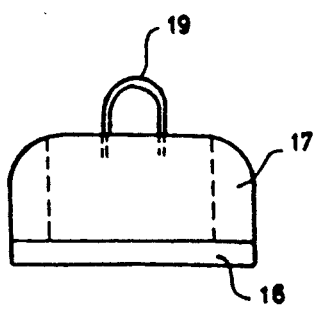
FIG. 4 is another side view of the gear mount ring illustrating the detent latching loop.
Figure 5:
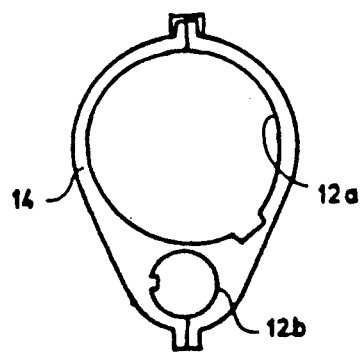
FIG. 5 illustrates the motor mounts.

FIGS. 2-4 show details of gear mount ring 17, including an internal gear ring 16, a detent latching loop 19 and a set screw 18. FIG. 5 illustrates the particular features of motor mount 14 including a through bore 12A for receiving motor 11 and a through bore 12B by which mount 14 is secured to rod 20. The ends of mount 14 are clamped as illustrated.

Figure 6:
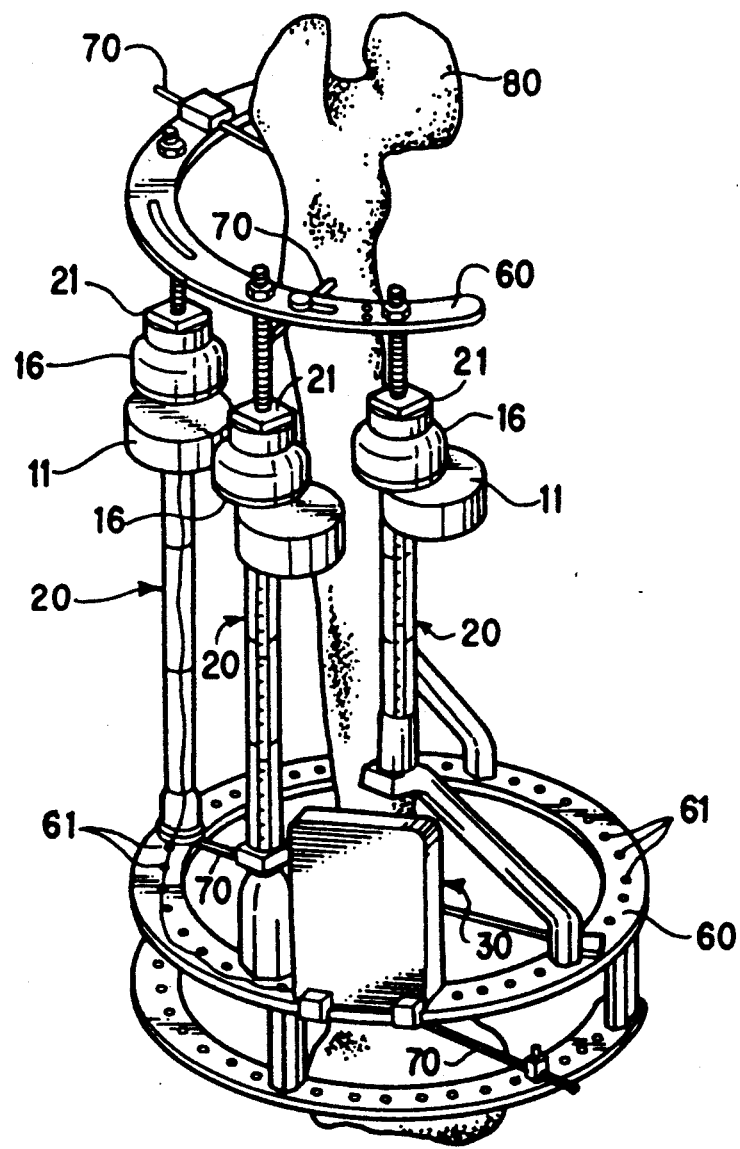
FIG. 6 illustrates the overall autodistractor/compressor/torsioner system according to the invention.

FIG. 6 illustrates the overall autodistractor/compressor/torsioner system 50 according to the invention. This system includes a plurality of support members 60, preferably in the form of perforated rings. Rings 60 include holes 61 in which a plurality of graduated telescopic rods 20 are secured in order to interconnect support rings 60. A plurality of pins 70 are attached to support members 60 and pass through the bone 80 of a patient. FIG. 6 shows a plurality of motors 11 and gear mount rings 17 mounted on nuts 21 of rods 20, these elements having the same structure as that illustrated in FIG. 1. The FIG. 6 system incorporates the elements of motor assembly 10, rod 20, controller 30 and sensor 40 shown in FIGS. 1-5. Controller 30 controls each of motors 11 mounted on the plurality of rods 20 and receives feedback from sensors 40 associated with each of motors 11 as described above in connection with FIG. 1.

Figure 7:
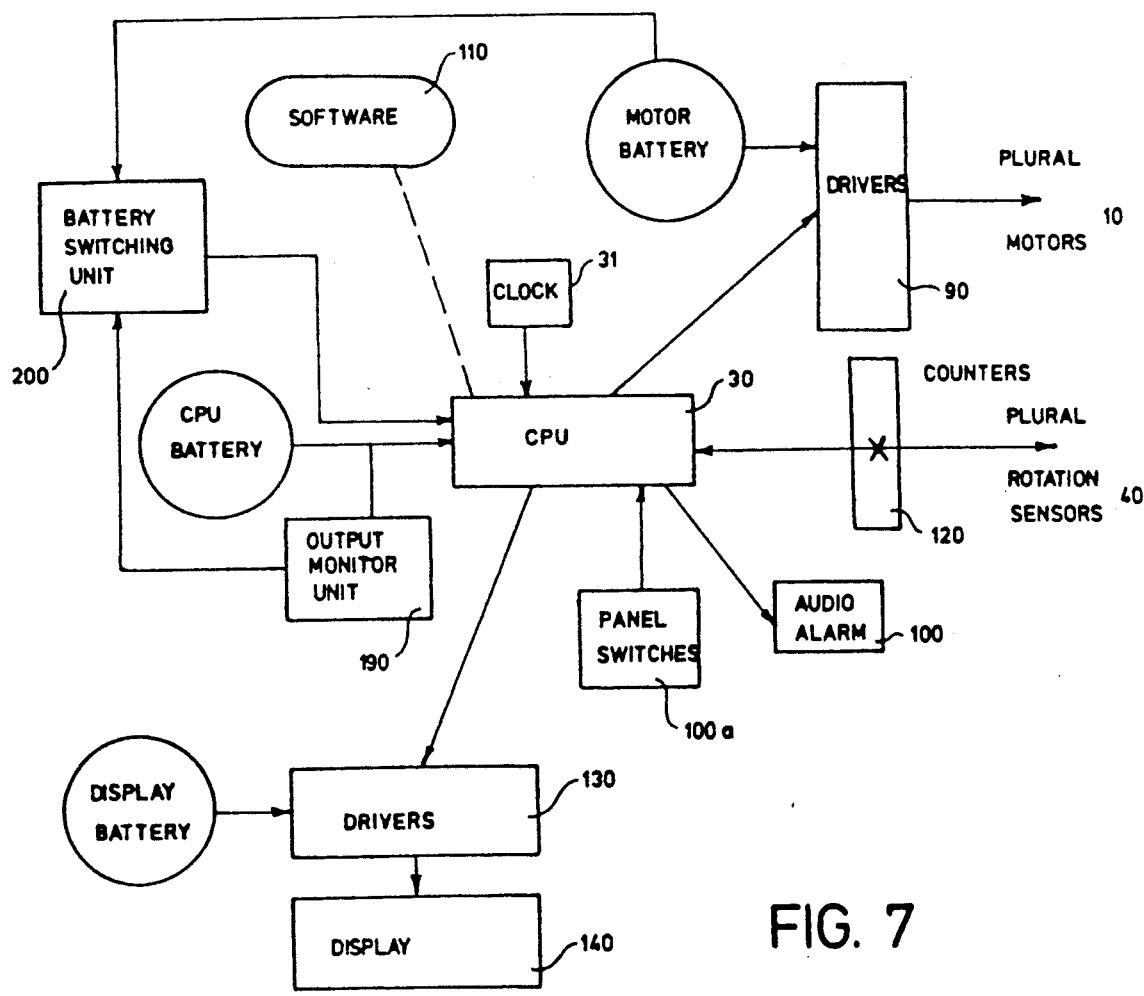
FIG. 7 illustrates the autodistractor/compressor/torsioner system in block diagram form.
Figure 8:
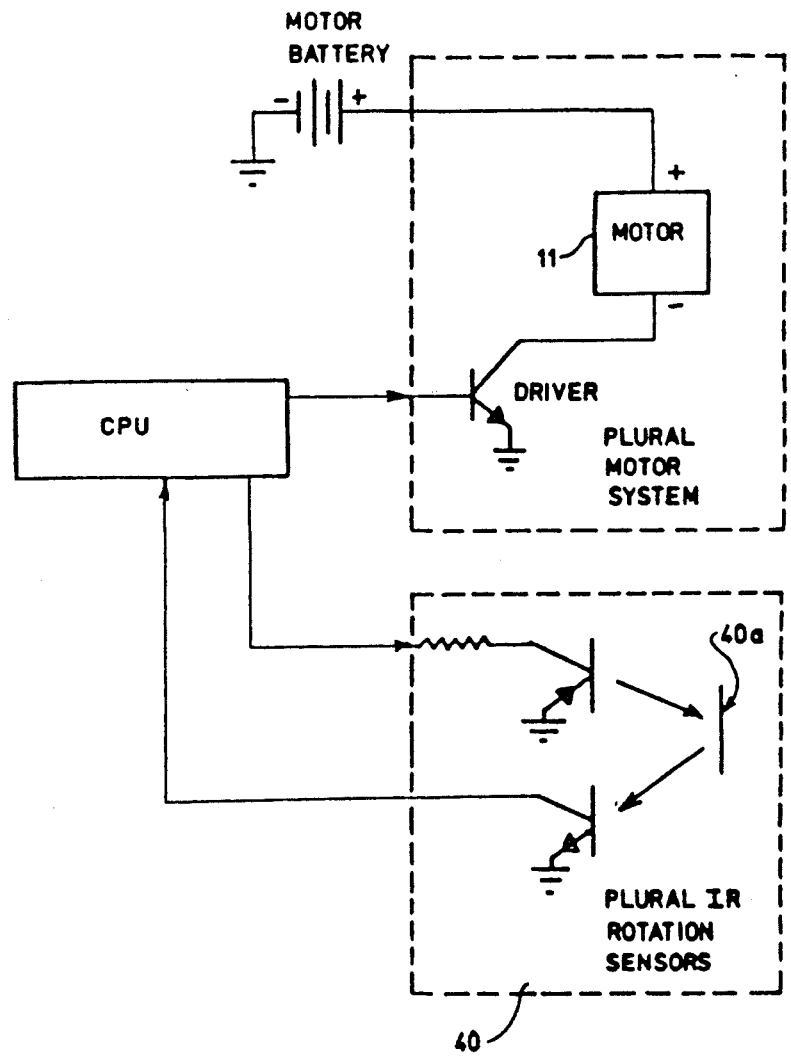
FIG. 8 illustrates further details of the system in partial block diagram format.

FIG. 7 and 8 illustrate the autodistractor/compressor/torsioner system in block diagram form. Controller 30 is in the form of a CPU synchronized with a clock 31. Software 110 controls controller 30 as described in detail below in connection with the flow charts of FIGS. 13-29. Sensor 40 provides feedback data regarding the actual position of rods 20; this data is stored in counters 120 and fed back to CPU 30. CPU 30 also provides data to display drivers 130 which drive display 140 to display the data in a format readily comprehensible to the doctor to enable determination of the progress of the overall treatment. Panel switches 100A include a display switch to control actuation of display 140. CPU 30 also provides output signals to drivers 90 for motors 11 to control the stepwise adjustments of rods 20.

As shown in FIG. 7, an output monitor unit 190 monitors the output from the CPU battery. If this output level falls below a predetermined threshold, monitor unit 190 sends a signal to battery switching unit 200 which is connected to the motor battery. This signal provided by monitor unit 190 to switching unit 200 causes unit 200 to switch the output from the motor battery to CPU 30. This insures continued supply of power to the CPU and provides protection against system failure in the event of failure of the CPU battery.

With reference to FIGS. 13-29, the operation of the automatic distractor/compression/torsion system according to the invention, is as follows.

OVERVIEW

The setup program is designed to operate on a personal computer (PC). This allows the doctor to customize the software on the microcontroller 170 for each particular distraction/compression/torsion case. The setup program will ask for and accept input on the number of motors, the process, i.e., compression, distraction or torsion, the number of millimeters movement per day, the number of times the motor will advance per day to achieve the required movement per day and the total movement required for the overall treatment. The setup program also collects information regarding the patient's name, doctor's name, chip number, date and other relevant information. Hard copies are generated of all inputted information to allow the doctor to verify the input, identify the microprocessor, (CPU 30) record the settings for patient records, and keep other necessary records.

After the microcontroller software has been downloaded into the microcontroller 170 memory and verified and the microcontroller 170 has been inserted into the electronics assembly, the software performs an initial check to be certain the electronics system is connected appropriately and the right chip has been inserted. If not, the software will trigger an alarm and an error code will be displayed.

If no error exists, the doctor can then actuate the start switch. The system will advance the motors and check to be certain all the motors are functioning properly. If not, the software will shut down the motors, display an error code and trigger the alarm.

Thereafter, the software controls the movement of each motor and tests to be certain that the motor is advancing the gear the amount established in the setup program via a feedback system. The advancement tests are run on a continuing basis to prevent a "runaway" or stalled motor condition. The system will shut down the motors, display an error code, and trigger the alarm if an advancement error is detected.

The software also monitors the current supply from the batteries to the central processing unit CPU 30 having EPROM microcontroller 170 installed therein, display and motors. If the current supply is low to the CPU 30, display or motors, the software will shut down the motors, display an error code and trigger the alarm. If the current to central processing unit 30 is low, the software will also shift the central processing battery supply to the motor power supply.

The software allows an operator to request a display at any time. The display will cycle through the position of each motor for each display request.

The software also allows transient electromagnetic fields to create a temporary current in the motor leads without shutting the motors down or triggering the alarm. The software further allows the doctor to manually put the system on standby for adjustments or other necessary interruptions.

The software shuts the motors down, displays the completion code, and triggers the alarm when the system has achieved the total required movement for the overall treatment procedure.

DETAILED DISCUSSION

Figure 10:
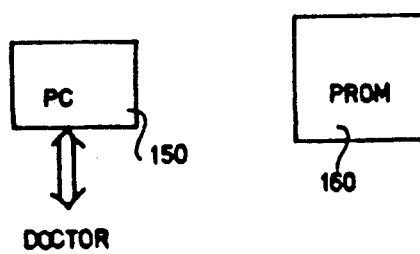
FIG. 10 illustrates the interactive set-up procedure.
Figure 11:
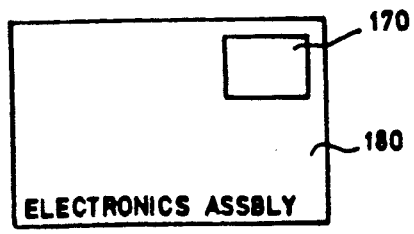
FIG. 11 shows a microcontroller.
Figure 13A:
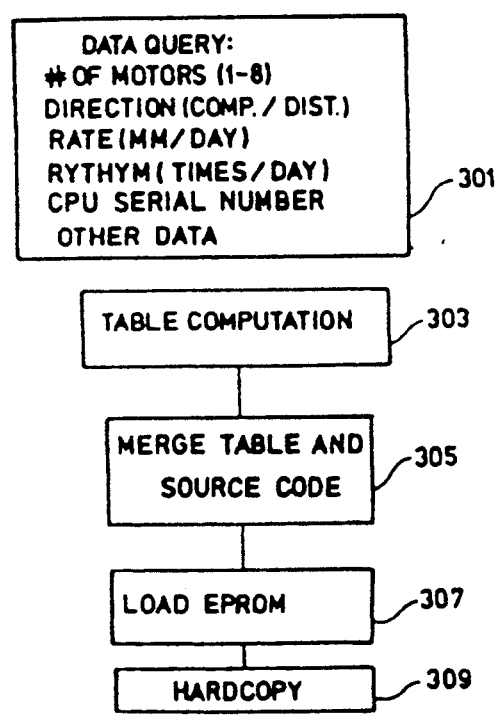
FIGS. 13-29 illustrate the operation of the automatic distraction/compression/torsion system according to the invention.
Figure 13:
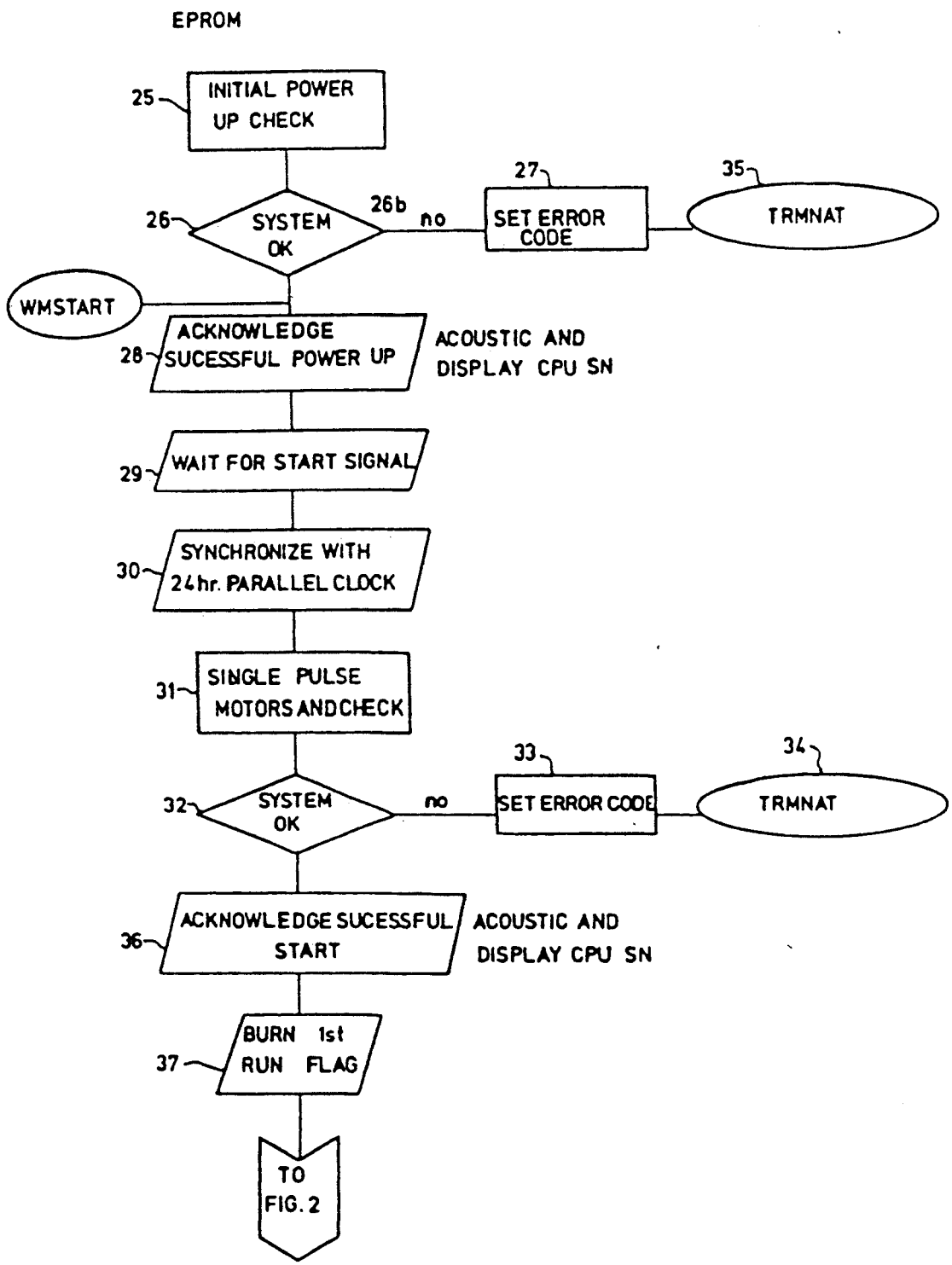
Figure 14:
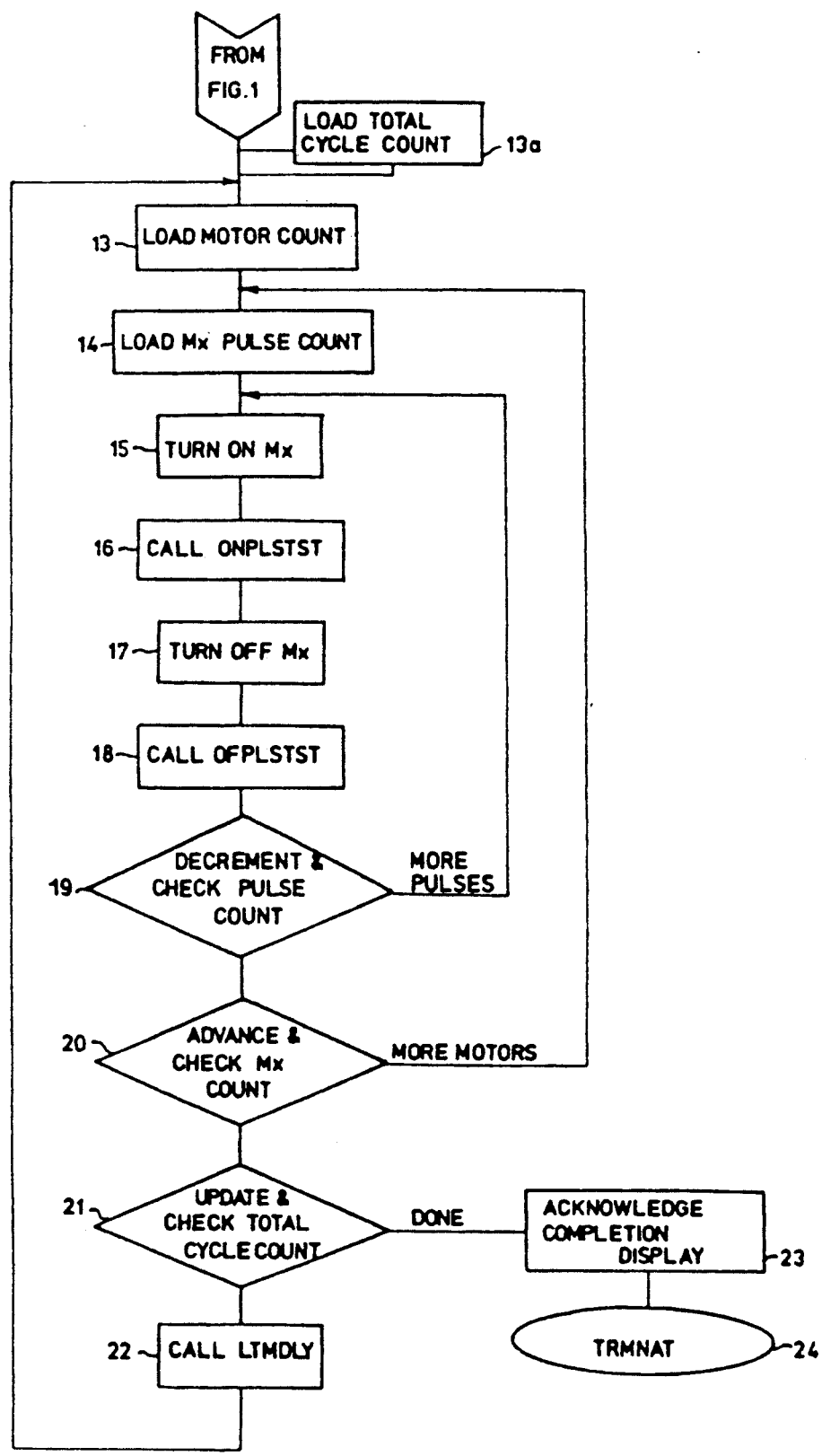
Figure 15:
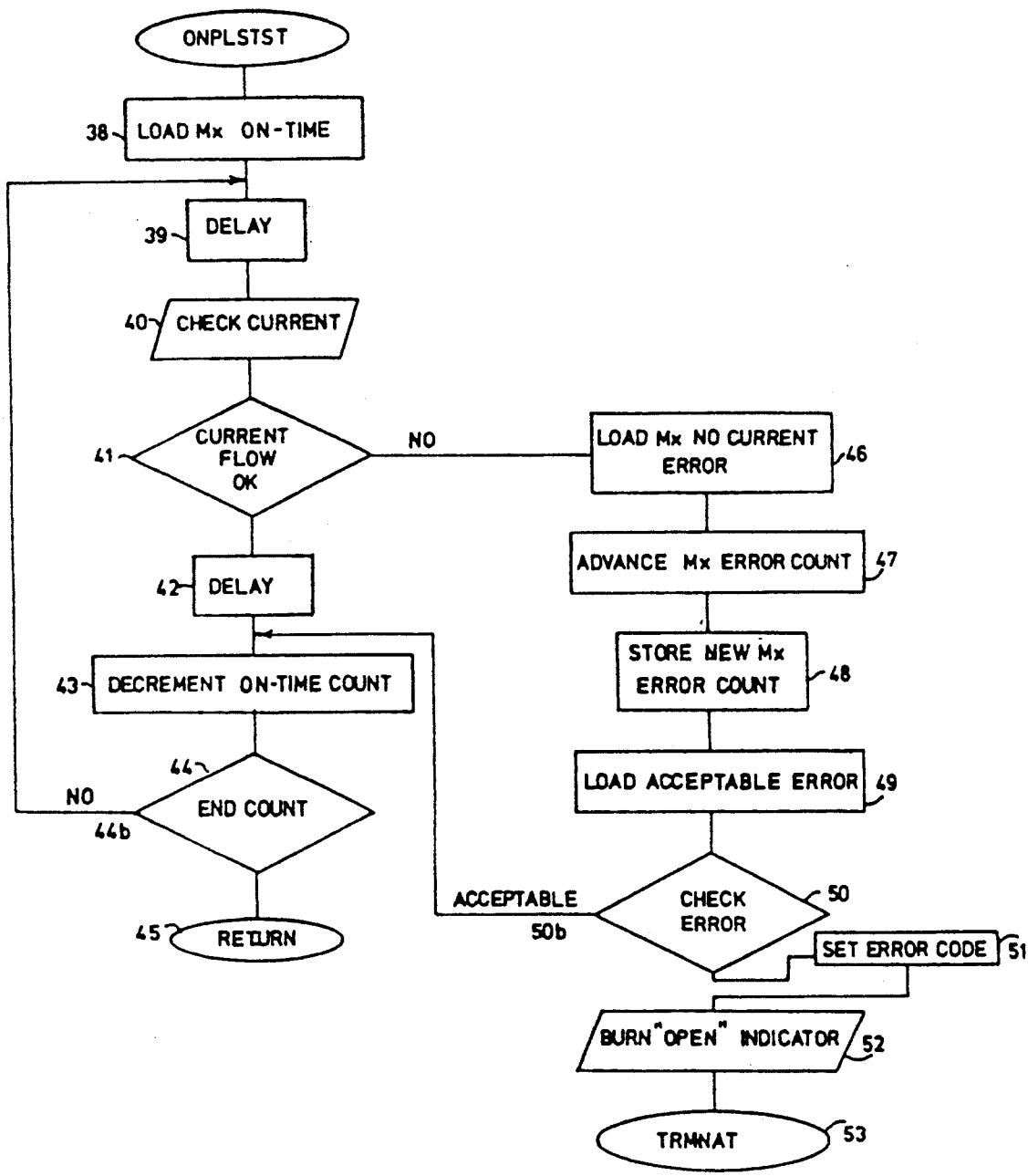
Figure 16:
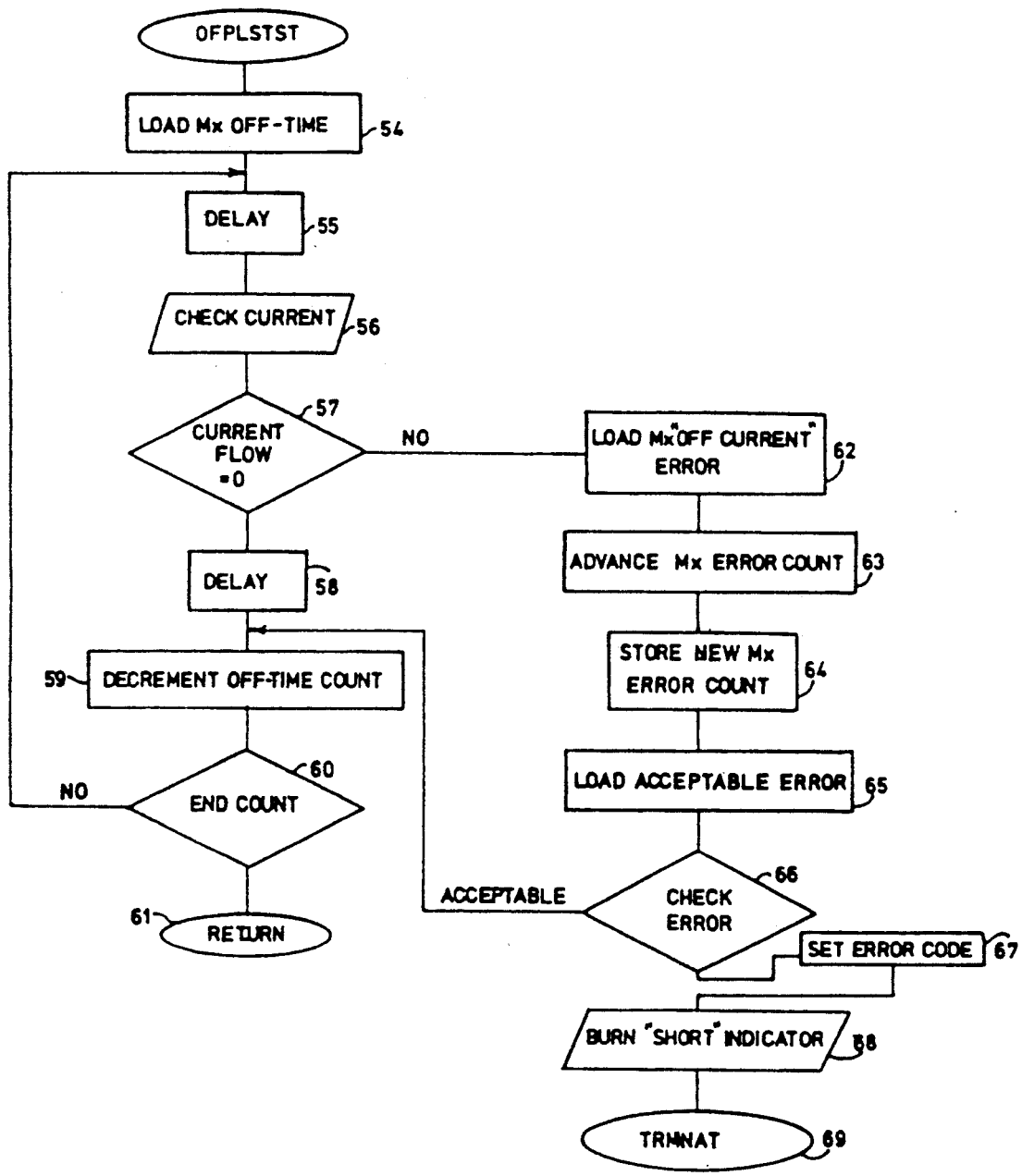
Figure 17:
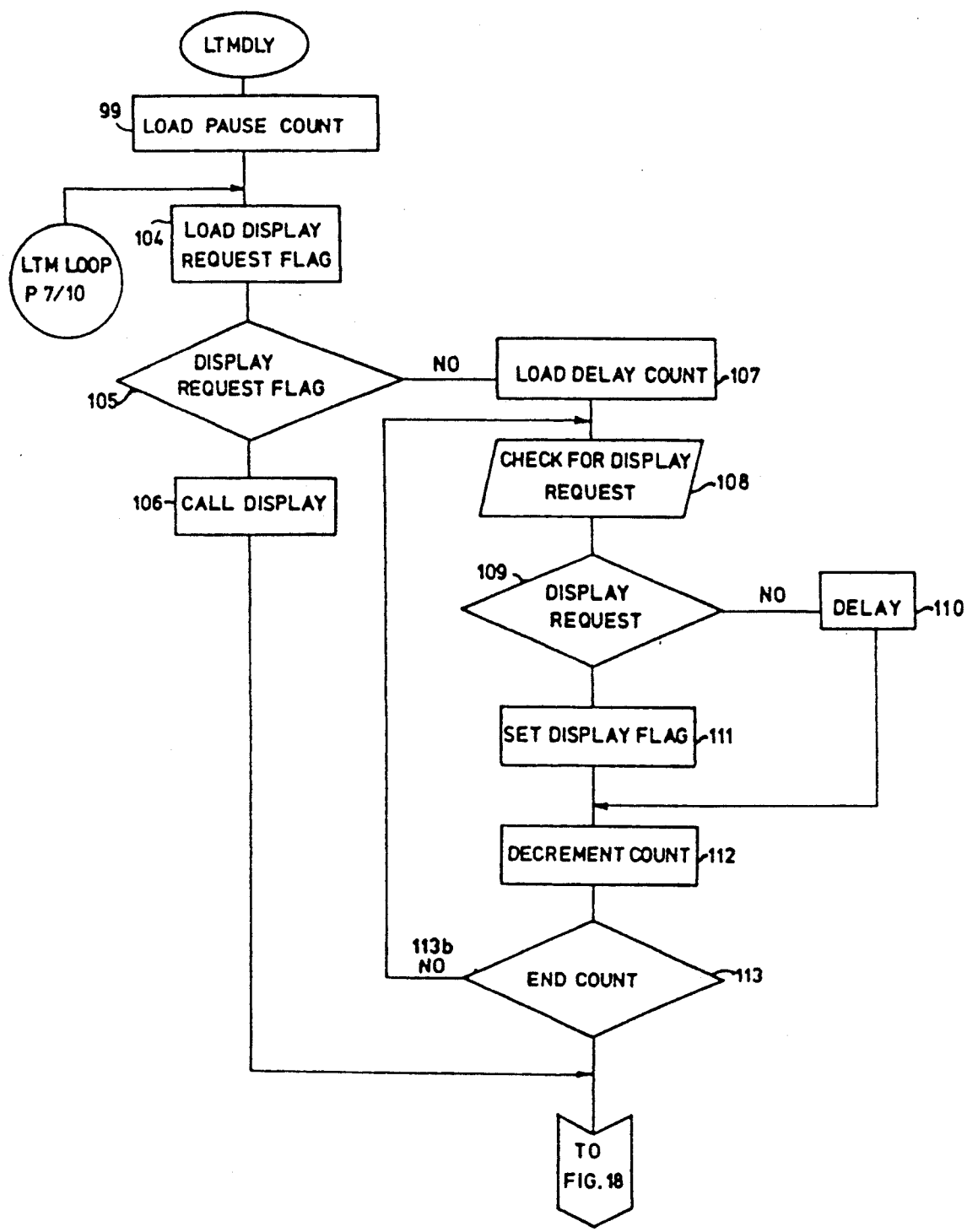
Figure 18:
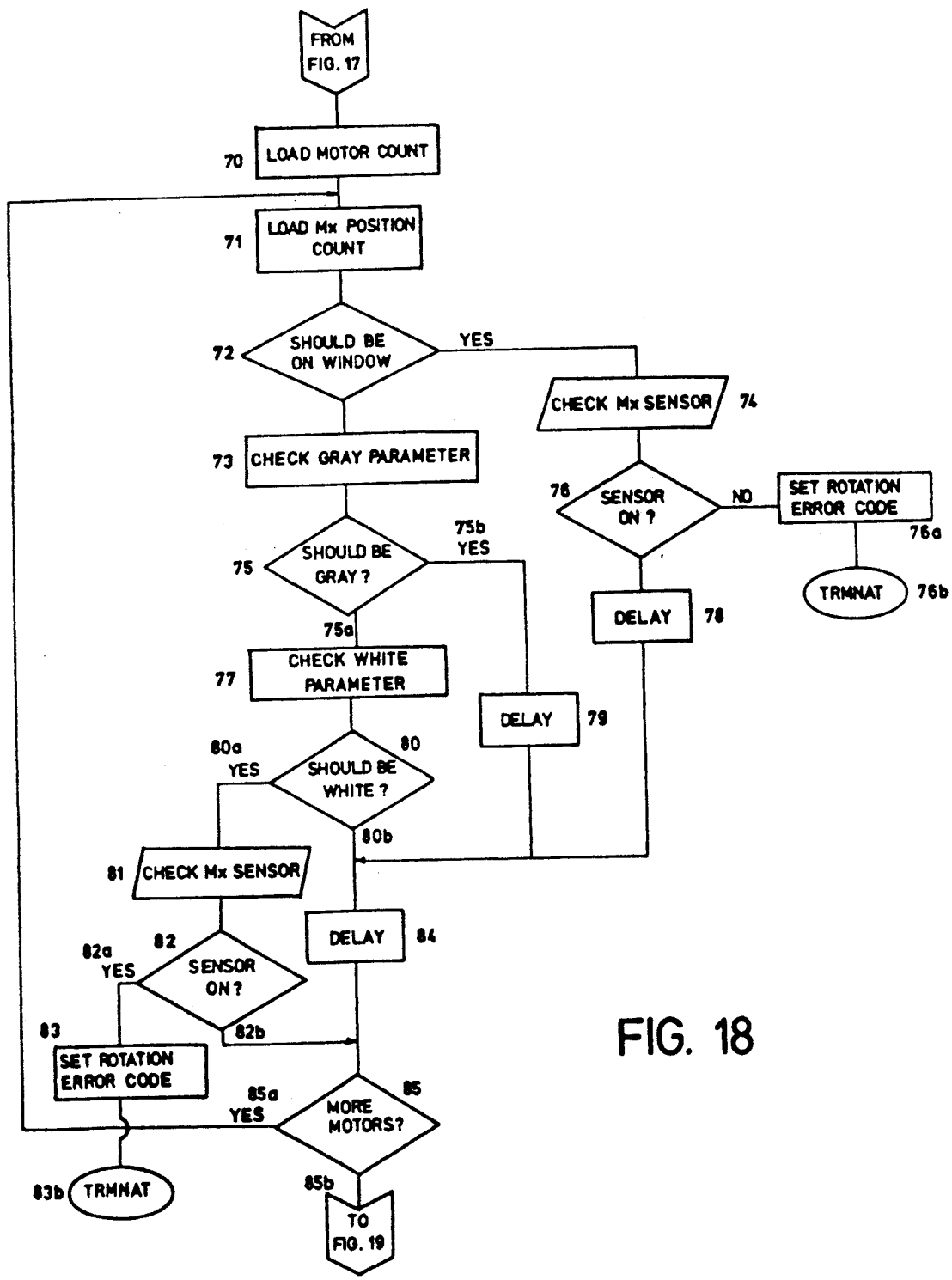
Figure 19:
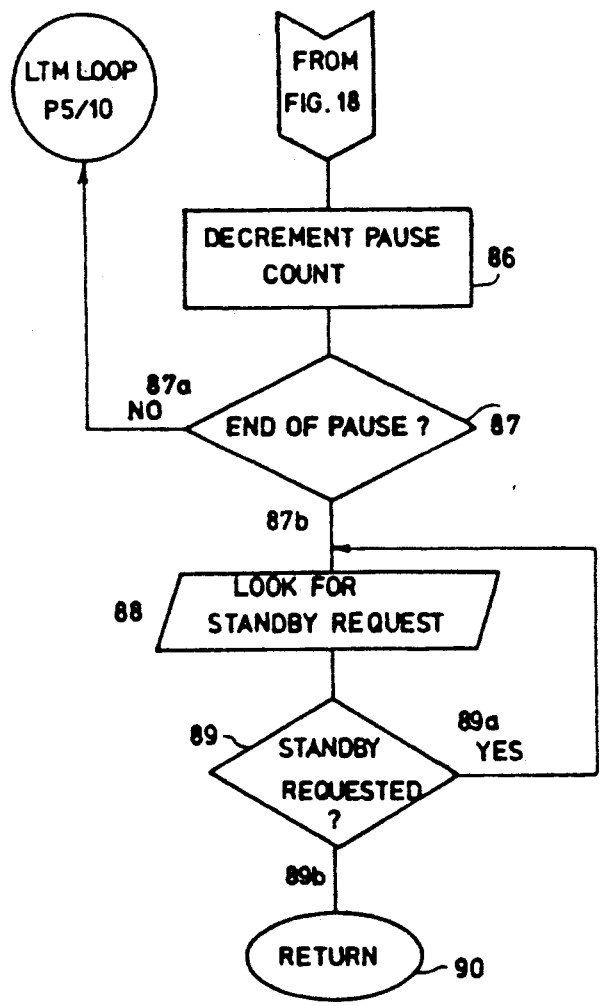
Figure 20:
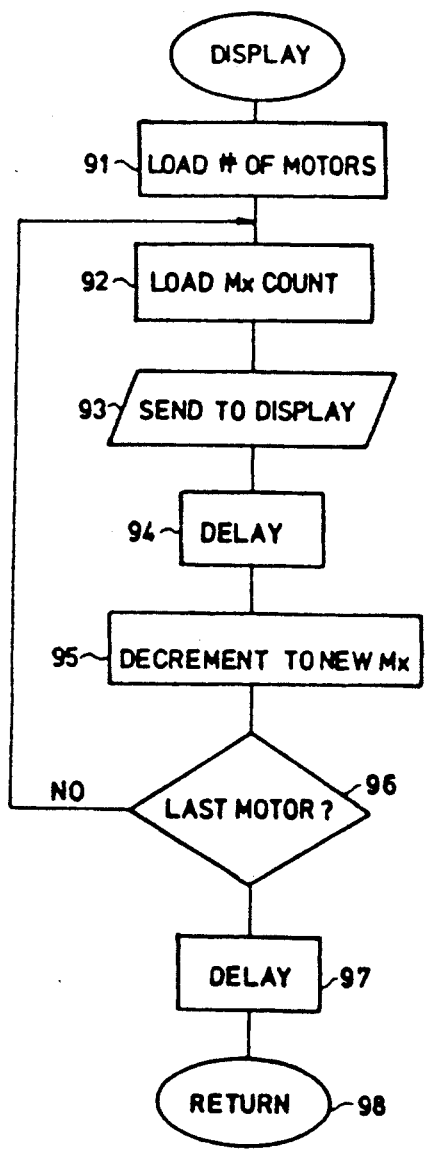
Figure 21:
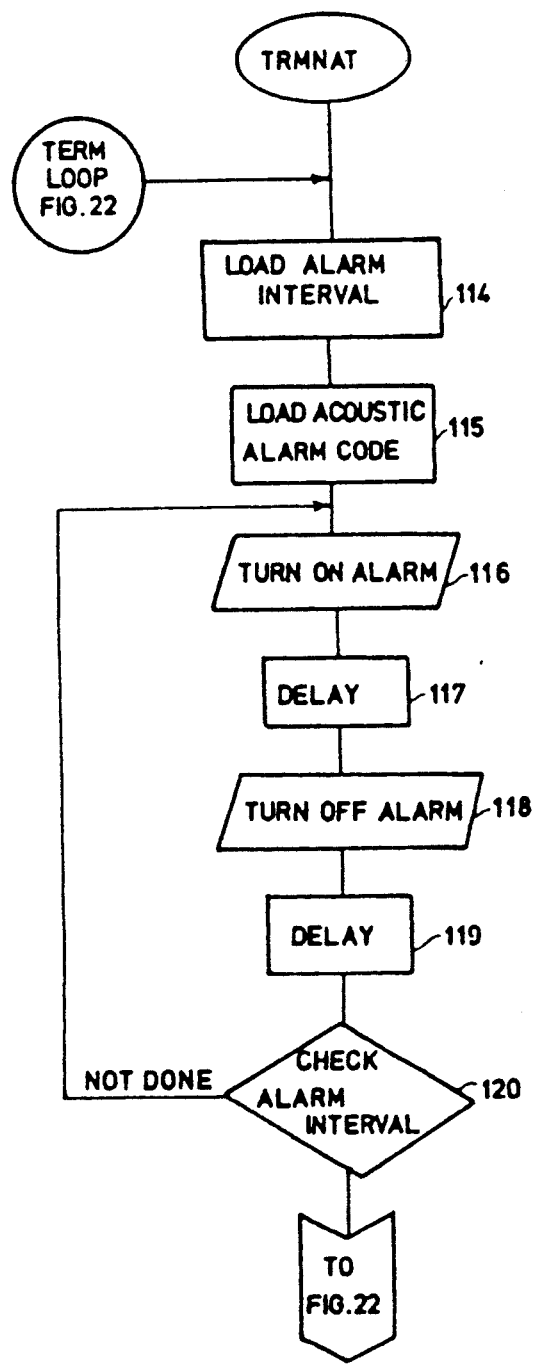
Figure 22:
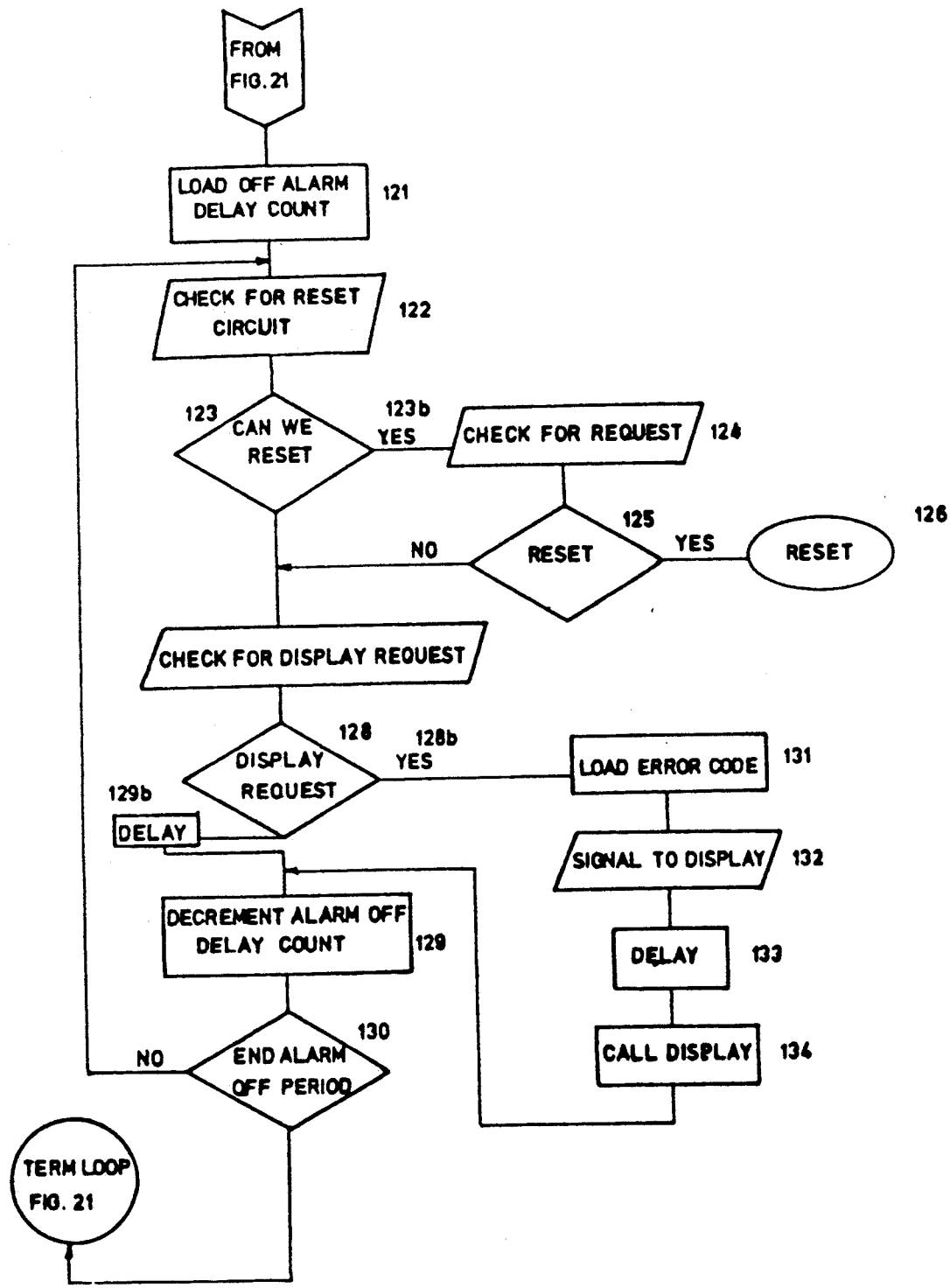
Figure 23:
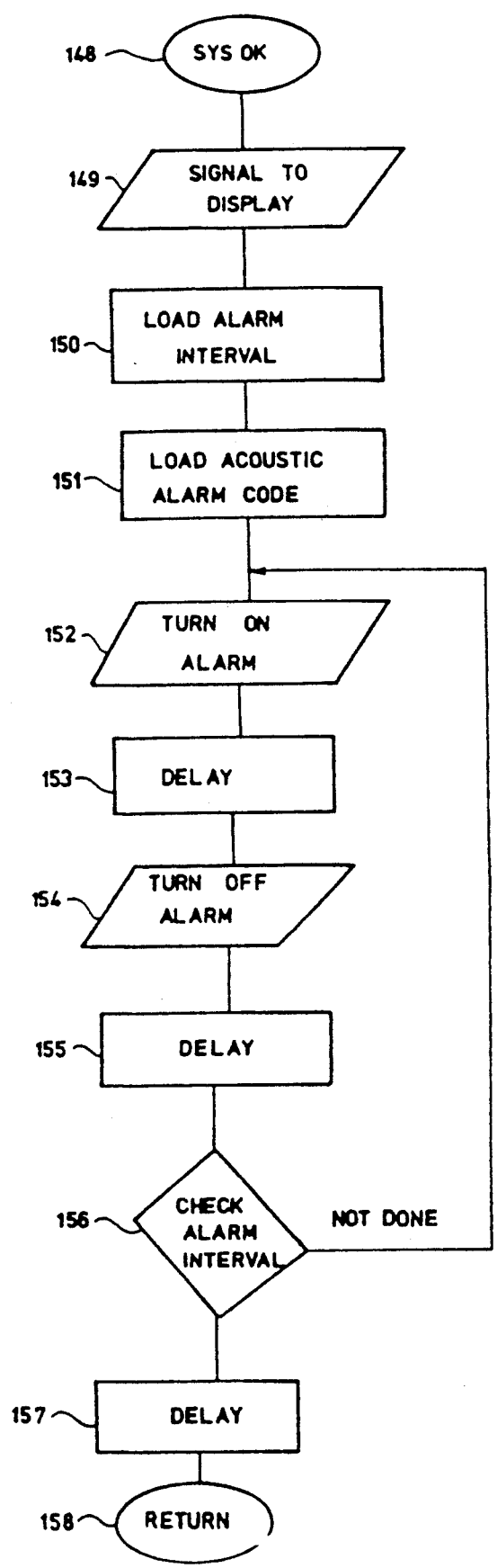
Figure 24:
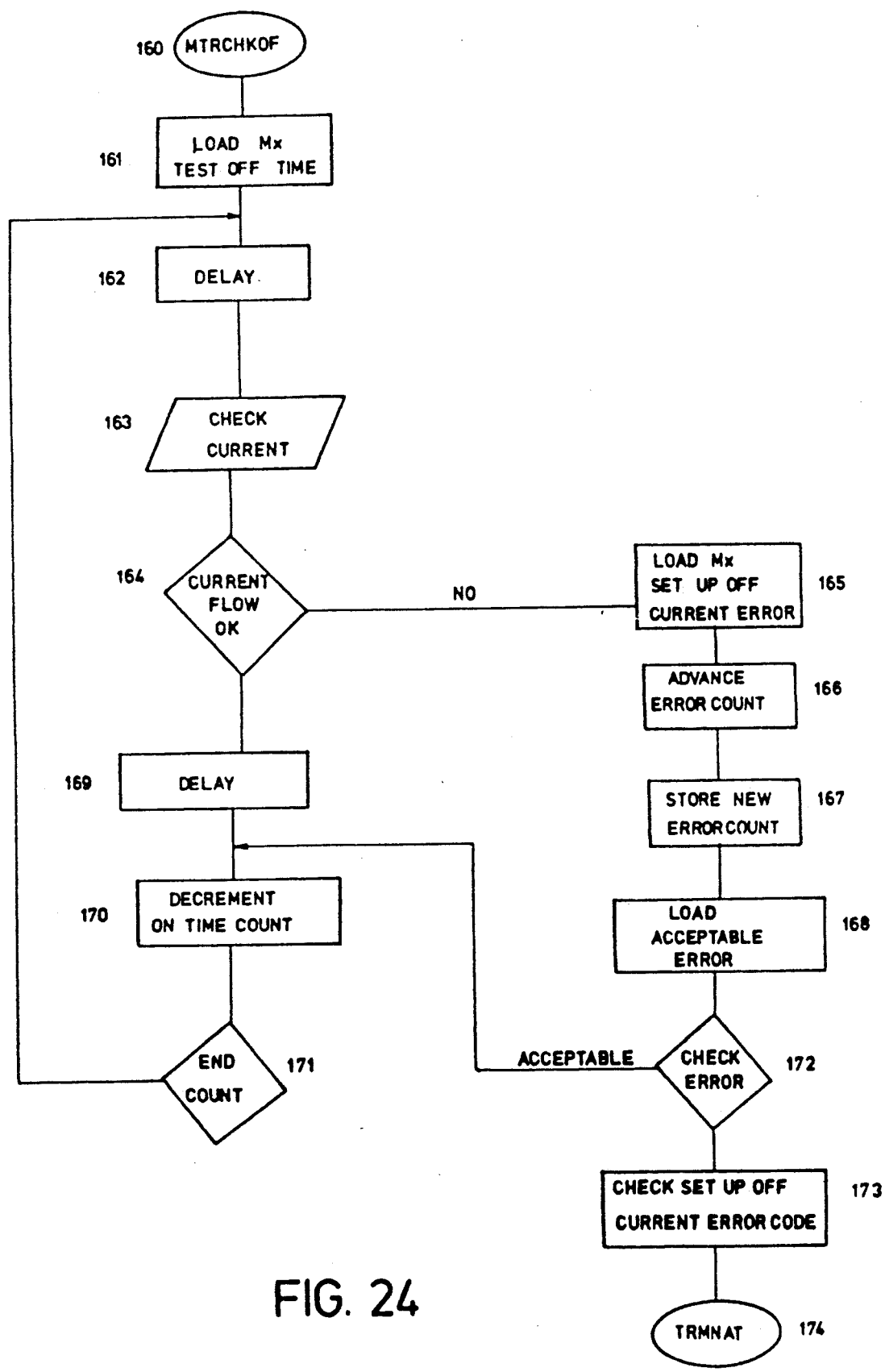
Figure 25:
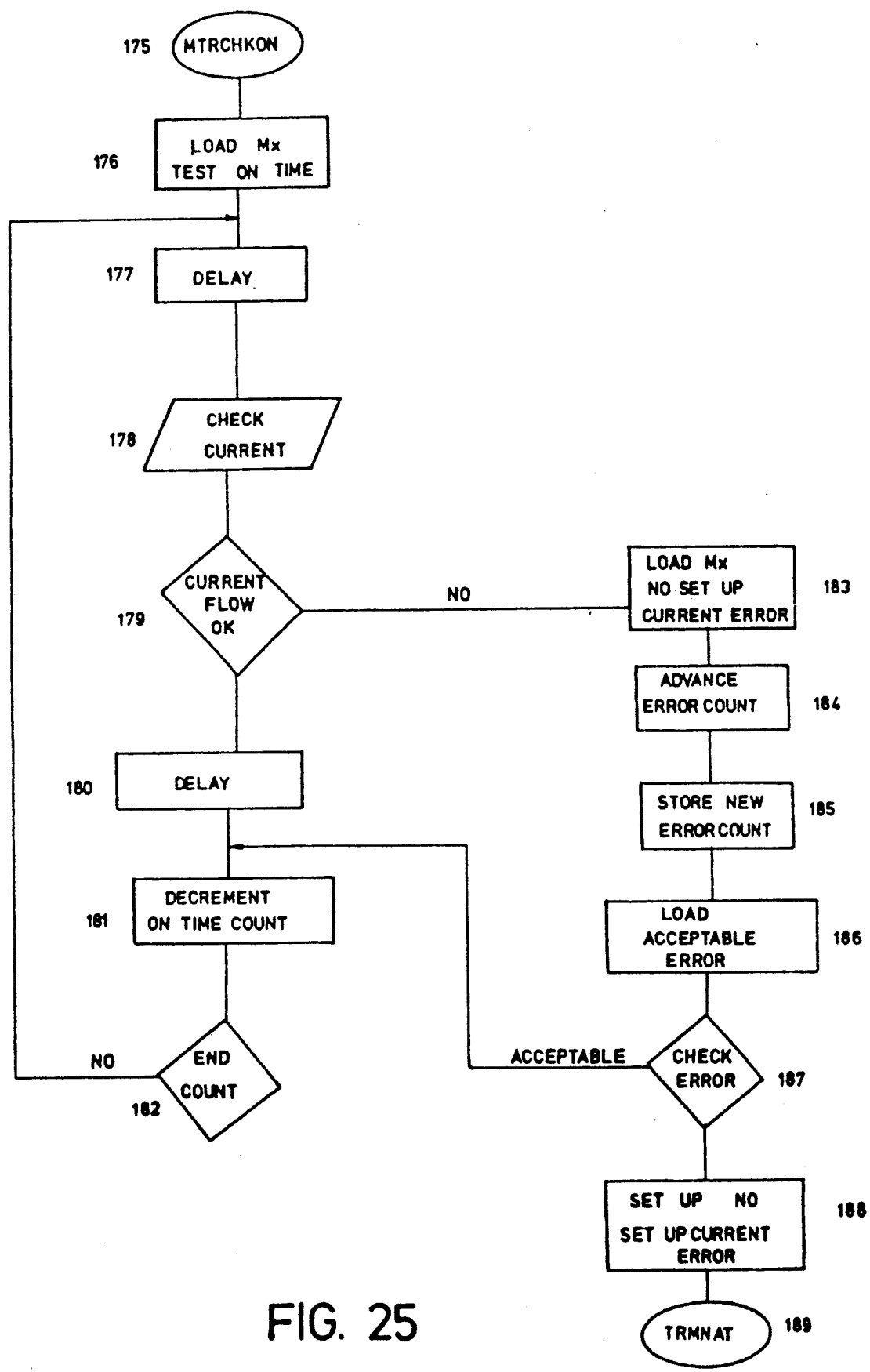
Figure 26:
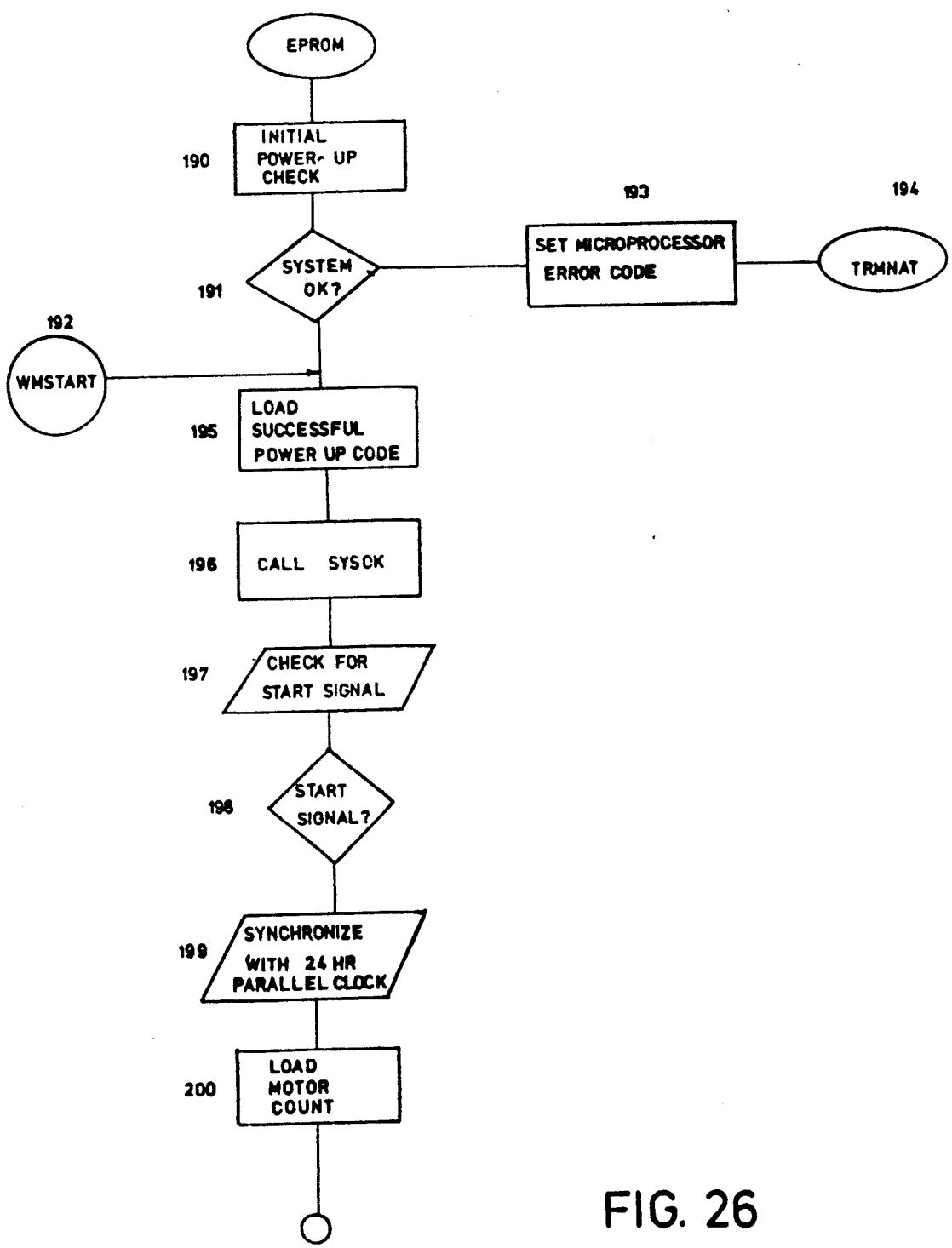
Figure 27:
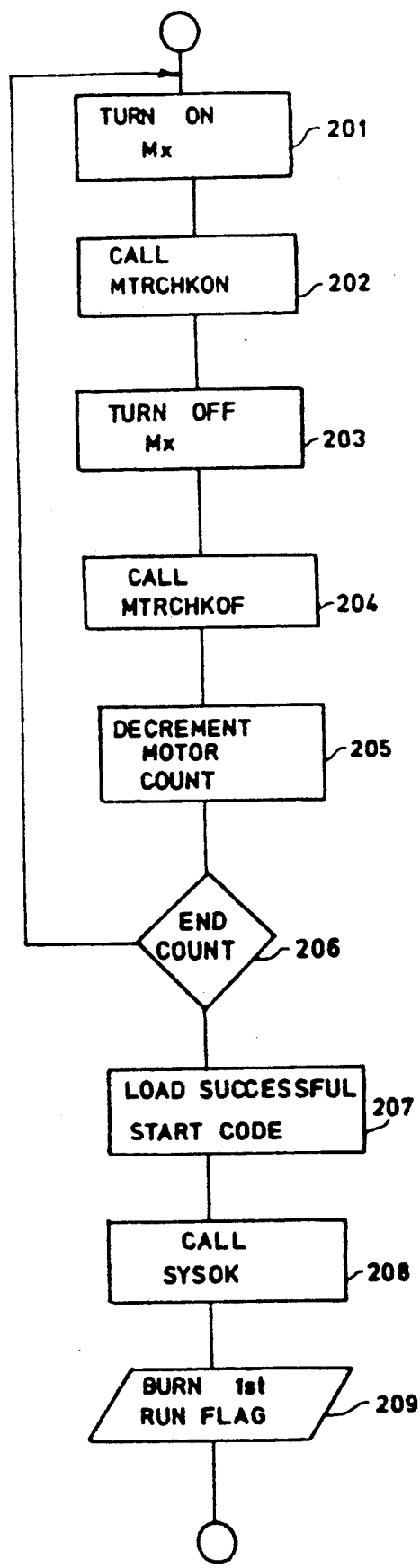
Figure 28:
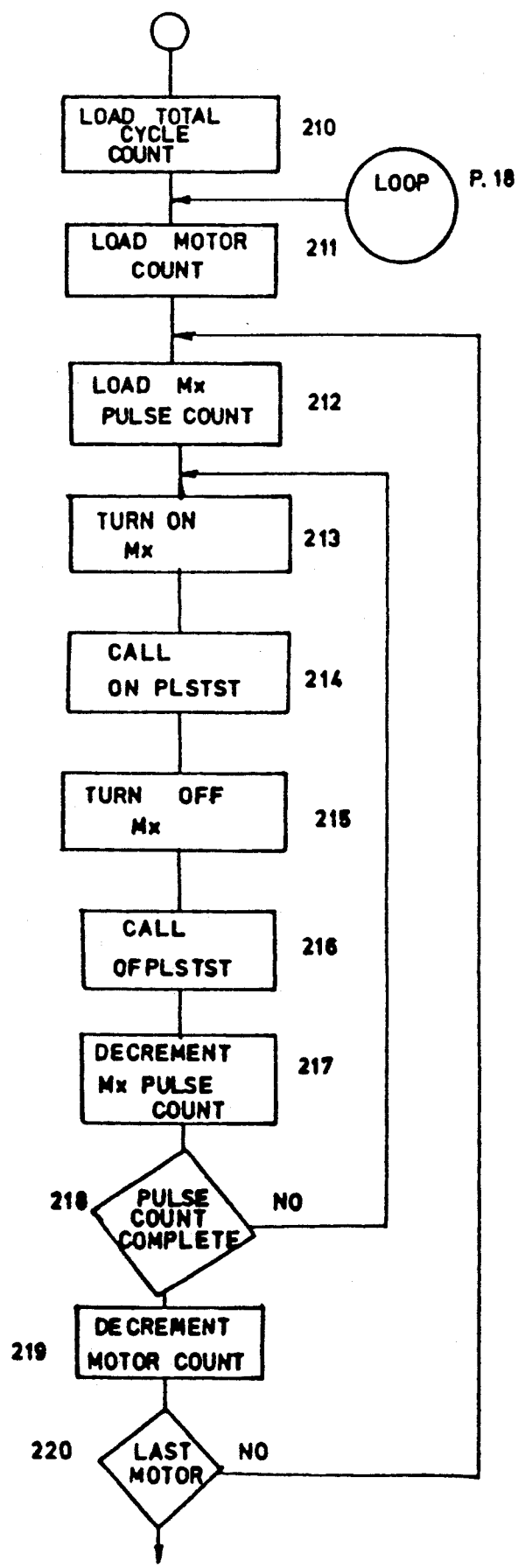
Figure 29:
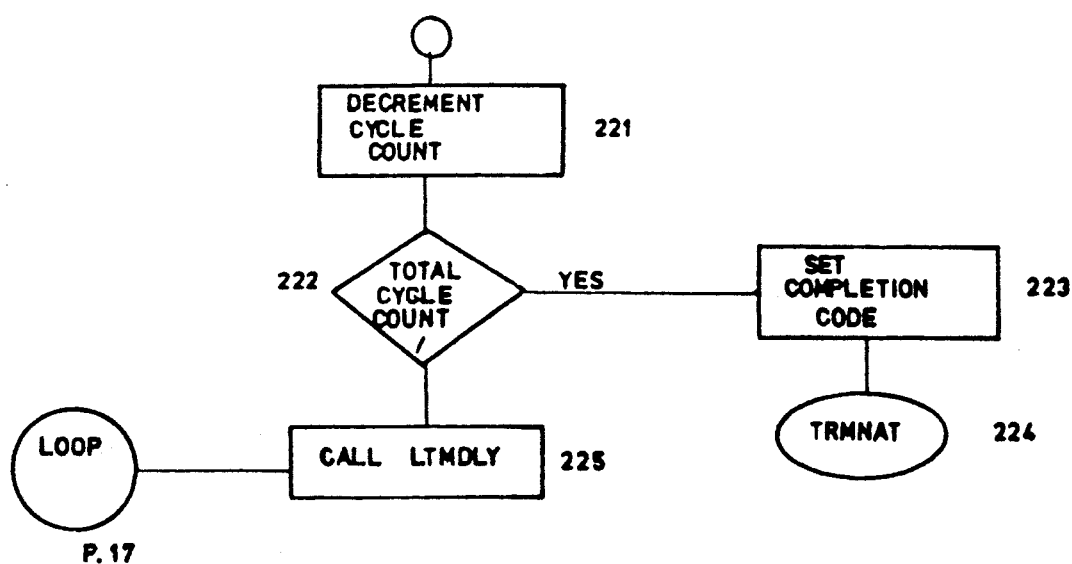

The ROMSET routine (FIG. 13A) is run on a personal computer (PC) by the doctor and sets up EPROM microcontroller 170 of the microprocessor (CPU 30). The doctor enters data in response to queries regarding the number of motors, the direction (compression, distraction or torsion), rate (mm/day), rhythm (times/-day), total movement required for the overall treatment and CPU serial number. The program then does a table computation at 303, based on the above-entered data, to generate a table of values to be called in software subsequently. This is done by converting the rate, rhythm and total treatment movement input by the doctor to data which the motors can employ-i.e., how many pulses are required to advance the motor through one advance cycle and the long term time delay imposed on the motors between advance cycles in order to achieve the movement equal to the required mm's/day at the given rhythm. Other miscellaneous data is also entered as discussed below. This table is then merged with the source code, 305 and further routine processing is done to load the EPROM at step 307. As noted, hard copy can also be generated at 309. FIGS. 10 and 11 illustrate a procedure for setting up or loading the EPROM microprocessor (CPU 30) via a PC 150, a PROM 160 and a microcontroller 170 which ultimately is inserted into an electronics board or assembly 180. After this loading procedure, microcontroller 170 is inserted into board 180 which in turn is installed in CPU 30. By reprogramming microcontroller 170, in the manner discussed above, the doctor is able to design a new treatment procedure as desired.

After the EPROM is programmed and installed on board 180, operation may begin. In the EPROM routine, initially, at step 25, a check is done to determine whether the system is operating properly and whether the correct chip (i.e., board 180 containing microcontroller 170) has been loaded into CPU 30. If no, an error code is set and a termination routine TRMNAT (to be described in detail below) is called. If yes, at 28 a successful powerup is acknowledged via an acoustic signal and a visual display. At 29, the system waits for the doctor to flip a start switch and, thereafter, at 30, the CPU clock is synchronized with the clock in the electronics assembly 180. At 31, a single pulse is sent to each of the motors and a check is done to be certain all motors are properly connected. At 32, if the system is not indicating proper functioning, an error code is set, and the termination routine TRMNAT is called. If the system is indicating proper functioning, this is acknowledged at 36, with an acoustic alarm and a visual display occurring. At 37, a first run flag is burned by burning a fuse in the electronics assembly.

At 13a, the total cycle count (i.e., the number of advance cycles to achieve the total treatment movement) is loaded, and at 13, the motor count (number of motors, e.g., 4) is loaded. At 14, the Mx pulse count (i.e., the number of pulses required to cause the particular motor to step the required amount at each particular advance cycle throughout the treatment) is loaded.

At 15, a given motor is turned on by sending one pulse to advance the Mx motor one increment, and at 16 a routine ONPLSTST is called to certify that the motor is on. At 17, the motor is turned off, and at 18 a routine OFFPLSTST is called to certify that the motor is off.

At 19, the counter is decremented. If the count has not reached zero, steps 14–18 are repeated. This is repeated until the count equals zero.

Thereafter, at 20 the system moves to the next motor and repeats steps 14–19 until the count for this motor reaches zero. Step 20 ends when each of the motors have been put through steps 14–19.

At 21, the CPU memory is updated with data indicating that steps 14–20 have been completed for each of the motors.

At 22, routine LTMDLY is called. This is a long-term delay routine which imposes a delay on the motors between advance cycles carried out by steps 14–20. This means all of the motors are stepped through one advance cycle, and then the long-term delay occurs. Then, each motor is again stepped through one advance cycle. The process is repeated until step 21 indicates the overall distraction, compression or torsion treatment is completed. At 23, an acknowledgment that the procedure is completed is displayed, and at 24 the termination routine TRMNAT ends the procedure.

Figure 9:
FIG. 9 illustrates a typical pulse supplied to a digital motor.

The subroutine ONPLSTST (on pulse test) is as follows. At 38, the time the motor is to be on is loaded, as obtained from the table generated during the ROMSET program. At 39, a delay is imposed to avoid checking the current pulse at the beginning of the pulse to avoid problems because of initial abnormalities. FIG. 9 shows a typical pulse, with readings from region B being avoided. The exact delay is set depending upon the type of digital motor employed.

At 40, the current flowing to the motor is checked. At 41, it is determined whether the current flow meets an acceptable limit. At 46, if the current flow is not acceptable, the "no current" error count is located. At 47, the error count is advanced by 1 to account for new "no current" error. At 48, the new "no current" error count is loaded in the memory. At 49, the acceptable error established in the ROMSET program (i.e., how many transient errors will be allowed before the movement of the system is terminated, such as 50 or 100; this allows flexibility so the doctor can make a determination depending on the environment of the patient). At 50, the new "no current" error count is checked, and a determination is made regarding whether it is below the maximum established as too many errors. At 52, if the error count is above the maximum number of allowable "no current" errors, the system physically burns a fuse designated the "open" indicator to show that, for some reason, there has been "no current" to the motor when there should have been current more than a maximum number of established times. Possible causes of the "no current" condition could be an open circuit or extensive interference from an external electrical field. At 50b, if the error count is below the maximum number of allowable "no current" errors, the system loops back prior to DECREMENT ON-TIME COUNT and the process is continued.

At 42, if the current flow is acceptable, a delay is imposed to match the time use for a "no current" decision.

At 43, the on-time count is decremented. For example, if the Mx on-time was 3 cycles through this loop, then, after the first time through this routine, the on-time count is changed to two. At 44, a check is made to determine if it is the end of the count loaded in load Mx ON-TIME (38). At 45, at the end of the count loaded in load Mx ON-TIME 38, a return is made to the EPROM program at step 17. At 44b, if the system is not at the end of the count loaded in load Mx ON-TIME, the system loops back through the routine as shown. At 51, the "no current" error code is set into the error code memory.

The subroutine LTMDLY (long-term time delay) at 99 loads the total count for the pause (e.g., 2,000) between motor movement cycles set in the ROMSET program. This will be dependent upon how many times/day the doctor desires the system to advance. At 104, the display request memory bit is loaded. At 105, it is determined whether a display request flag is in the display request bit, and, if so, at 106, the DISPLAY subroutine is called. If there is no flag, at 107, the delay count is loaded. This delay count is set in the ROMSET program to match the time required for the display subroutine.

At 108, an I/O check is made for a display request. At 109, a check is made whether the display button has been pushed and the associated electronics hardware activated. If a display request exists, at 111, the display flag is set. If no display request has been made, at 110, a delay is imposed to match the time required to set the flag.

Figure 12:
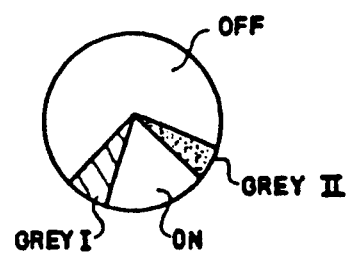
FIG. 12 illustrates grey and white parameters used in the long-term delay subroutine.

At 112, the count is decremented to account for advancement of one cycle. At 113, a check is made as to whether the value now stored in the delay indicates the end of the count. If not, at 113b, the system cycles back through the loop. If it is the end of the count, at 70, the number of motors is loaded. This is determined from the table established in the ROMSET program. At 71, the motor position count (for example, motor 1) is loaded from the table established in the ROMSET program. At 72, it is determined whether this position count indicates the sensor should be ON. At 74, if the sensor is ON, the sensor is then checked at 76. If yes, at 78, a delay is imposed to match the time it takes to check other alternatives. If the sensor is OFF, at 76a, the rotation error code is set. If the sensor should not be ON based on the position count of the motor, at 73, the position parameters are loaded for the grey 1 area, i.e., between 5 and 10 is grey 1. This is illustrated in FIG. 12. At 75, a determination is made as to whether the position count corresponds to a grey 1 area. This is done by comparing the actual position count to the range for grey 1, e.g., 5-10. Thus, if the actual position count is 6, this corresponds to a grey 1 area, whereas a count of 2 would not. At 75b, it is determined that the system should be in the grey 1 area, and at 75a, it should determined that the system is not be in the grey 1 area. At 79, a delay is imposed to match the time required for other checks.

At 77, the position parameters are loaded for the white area (see FIG. 12). At 80, a determination is made as to whether the system should be in the white area according to the position count. Step 80a corresponds to a count indicating a white area, and 80b indicates a count not quite corresponding to the white area. At 81-82b, a check is made as to whether the motor sensor is ON. At 83, if the sensor is ON, the rotation error code is set. At 84, a delay count is imposed to match the time required for the computer (CPU 30) to do other checks. At 85-85b, a determination is made as to whether all of the motors have been checked. At 86, the pause count is decremented to account for advancement of one cycle. At 87-87b, a determination is made as to whether the system is at the end of the total established pause count. At 88, the system looks for a standby request which is a jumper connected by the doctor. At 89-89b, a determination is made as to whether the standby jumper has been connected. At 90, the system is returned to load motor count (step 13).

Turning now to the subroutine DISPLAY, if the system is at the end of the count, at 91, the number of motors is loaded based on the table established by the ROMSET program. At 92, the Mx distraction count is loaded. In other words, this count indicates how far the motor has distracted the telescopic rod. At 93, an indication of the amount of the distraction is sent to the display. At 94, a delay is imposed to allow the doctor to view the distraction distance. At 95, the system decrements to the next motor sequentially, i.e., the system moves from Mx=M2 to Mx=M1. At 96, a determination is made as to whether this is the last motor, and at 97, a delay is imposed. At 98, a return is made to step 70 to the number of motors or alternatively the display subroutine can be called to allow the doctor to view the current distraction distance as discussed below.

With respect to the subroutine RESET, at 141, the software error flags set earlier which caused the system to call the TRMNAT subroutine are cleared. At 142, the system checks for hardware error flags. All blown fuses must be replaced before resetting the system. Blown fuses show as a hardware error flag. At 143-143b, a check is made as to whether the hardware flags are OK. At 144, the "not ready" code is set for the display. At 145, the alarm interval in the TRMNAT subroutine is changed. At 146, the system goes to the TRMNAT subroutine. At 147, the system goes back to just prior to step 28, which is the acknowledged successful power-up step in the EPROM routine.

Regarding the TRMNAT subroutine, at 114, the alarm interval set in the ROMSET program is loaded, and at 115, the acoustic alarm code (alarm sound) is loaded. At 116, the alarm is turned on by sending current to the alarm. Step 117 imposes a delay to allow the desired length of sound. Step 118 turns the alarm off. At 119, a delay is imposed to allow the desired length of time between alarm sounds. At 120, a determination is made as to whether the alarm has been activated enough times to meet the alarm interval from step 114. At 121, an "off alarm" delay is imposed. This is set in the ROMSET program and represents a period of time between alarms. At 122, the system checks to determine whether the setup has a reset capability from the ROMSET program. At 123, the system determines whether a reset is acceptable. At 124, the system checks for a reset jumper in the electronics hardware. At 125, a determination is made as to whether the reset jumper is in place. At 126, the system goes to the RESET subroutine. At 127, the system checks for a display request, i.e., whether the doctor has pushed the button for the display. At 128, a determination is made as to whether display has been requested. If yes, at 131, the error code is loaded for the error which caused the system to go into the TRMNAT subroutine. At 132, the error code signal is sent to the display for viewing. At 133, a delay is imposed to allow the doctor sufficient time to view the code. At 134, the display subroutine is called to allow the doctor to view the current distraction distance. If no display request has been made, at 129b, a delay is imposed to match the time for the error code display and current distraction distance displays. At 129, the "alarm off" delay count is decremented, and at 130, a determination is made as to whether the end of the "alarm off" period is present based on the number loaded at step 121.

Steps 190-225 represent a more detailed or alternative version of the EPROM program. At 190, an initial power-up check is made to be certain that the chip is acceptable, and the RAM is checked. Also, a check is made to be certain that the correct chip has been inserted. At 191, a determination is made as to whether the initial power-up check indicates the system has checked out acceptably. If not, the microprocessor error code is set at 193, and at 194, the system goes to the TRMNAT subroutine. If the system is checking out acceptably, at 192, the WMSTART subroutine from the RESET subroutine is carried out. At 195, a successful power-up code is loaded. At 196, the SYSOK subroutine is called, which will provide an audio OK signal and display a successful power-up code. At 197, the system checks for a start signal (which is a hardware jumper). At 198, the system queries whether a start signal is present. At 199, the CPU clock is synchronized with an external clock to verify that the chip is functioning correctly.

At 200, the motor count is loaded, to indicate the number of motors set in the ROMSET program. At 201, motor x is turned on by supplying power to the motor. At 202, the subroutine MTRCHKON is called, which tests whether there is current to the motor and shuts the system down if not. At 203, motor x is turned off. At 204, subroutine MTRCHKOF is called, which tests whether there is no current to the motor and shuts the system down if there is current to the motor.

At 205, the motor count is decremented by 1. At 206, a determination is made as to whether this is the last motor. At 207, a successful start code is loaded. At 208, the SYSOK subroutine is called, and at 209, the first run flag is burned by physically burning a fuse which acknowledges the successful startup.

At 210, the total cycle count is loaded, which has been established in the ROMSET program and represents the total number of movements of the motor required to achieve the overall desired distraction for the entire treatment procedure. At 211, the motor count is loaded, which is the number of motors established in the ROMSET program. At 212, the number of pulses to be supplied by motor x is loaded; this number is also established in the ROMSET program. At 213, the motor is turned ON and at 214, the ONPLSTST subroutine is called. This latter subroutine checks to be certain there is current to the motor. There is a cumulative error counter which will cause the system to alarm and shut down if there have been too many times when no current is flowing during motor ON time. At 215, the motor is turned OFF. At 216, the OFPLSTST subroutine is called. This checks to be certain there is no current to the motor when the motor is to be OFF. There is a cumulative error counter which will cause the system to alarm and shut down if there have too many times when current is flowing during motor OFF time. At 217, the motor x pulse count is decremented. For example, if a total of 133 pulses were required, the pulse count would be decremented to 132 after the first time through. At 218, the system checks whether the required pulses (e.g., 133) have been sent. If yes, at 219, the motor count is decremented. At 220, a determination is made as to whether this is the last motor. At 221, the cycle count is decremented, and at 222, a determination is made as to whether the total required cycles for the overall treatment have been completed. If yes, at 223, the completion code is set, and the system proceeds to the TRMNAT subroutine. This latter subroutine causes the system to alarm and allows no further movement of the system. It also allows the doctor to view an error code for problems and display cumulative movements of the telescopic rods prior to system shutdown. It also allows the doctor the option of resetting the system after correcting any problem.

At 225, the LTMDLY subroutine is called. This allows the doctor to display cumulative movement of the telescopic rods. The system checks to be certain that the advancement nut has moved an amount equivalent to the amount expected based on the number of pulses sent to the motor within a specified range. This also provides a delay between motor movements.

With respect to the MTRCHKOF (motor check OFF) subroutine, the logic is the same as the OFPLSTST subroutine.

With respect to the MTRCHKON (motor check ON) subroutine, the logic is the same as the OFPLSTST subroutine.

Turning now to the SYSOK subroutine, at 49, the code is sent to the display, and at 150, the alarm interval is loaded to determine how many times the alarm will beep. At 150, the acoustic alarm code (alarm sound code) is loaded. At 152, the alarm is turned ON, and at 153, a delay is imposed to obtain the desired length of time. At 154, the alarm is turned OFF, and at 155, a delay is imposed to provide the desired time duration between beeps. At 156, a check is made as to whether the alarm interval is complete by keeping track of the number of beeps. At 157, a delay is imposed to allow the doctor or a technician sufficient time to review the code.

With respect to the OFPLSTST subroutine, this is the same as the ONPLSTST subroutine, with the exception that the system checks to be certain that current is zero rather than that current flow is sufficient.

It should be noted that the above description and the accompanying drawings are merely illustrative of the application of the principles of the present invention and are not limiting. Numerous other arrangements which embody the principles of the invention and which fall within its spirit and scope may be readily devised by those skilled in the art. Accordingly, the invention is not limited by the foregoing description, but is only limited by the summary or scope of the invention as described in this application.

We claim:

1. A medical apparatus, comprising:
   a plurality of support members;
   a plurality of rods interconnecting said support members and including adjustment means for enabling the rod length to be adjusted;
   means connected to said support members for securing said support members to a patient; and
   an automatic drive means for controlling said adjustment means of said plurality of rods, said drive means comprising at least one motor for incrementally adjusting the adjustment means of said plurality of rods to adjust the length of said rods, and a controller means for providing pulses to said at least one motor to control the incremental adjustments of plurality of rods and for storing information regarding the number of stepwise adjustments of said rod length of said plurality of rods by said at least one motor.

2. An apparatus for positioning an article, comprising:
   a plurality of support members;

at least one adjustable length rod interconnecting said plurality of support members and including an adjustment means for enabling said rod length to be adjusted;

means connected to at least one of said plurality of support members for securing said plurality of support members to said article to be positioned;

an automatic drive means for controlling said adjustment means for adjusting said length of said at least one rod, said drive means comprising at least one motor for incrementally adjusting the adjustment means of said at least one rod to adjust the length of said at least one rod; and controller means for controlling and monitoring the incremental adjustments of said at least one rod and for storing information regarding the number of adjustments of said rod length of said at least one rod by said at least one motor.

3. The apparatus of claim 2, wherein said controller means also stores information regarding an instantaneous number of stepwise adjustments performed by said at least one motor.

4. The apparatus of claim 3, further comprising feedback sensor means for sensing the amount of adjustment of said rod length of said at least one rod and providing data representing said sensed amount of adjustment to said controller means.

5. The apparatus claim 4, wherein said controller means comprises means for comparing said information regarding the instantaneous number of stepwise adjustments with said data representing said sensed amount of adjustment.

6. The apparatus of claim 4, wherein said feedback sensor means is an infrared sensor.

7. The apparatus of claim 4, wherein said feedback sensor means is a magnetic reed switch.

8. The apparatus of claim 3, further comprising display means, connected to said controller means, for displaying a representation of said information regarding said instantaneous number of stepwise adjustments of said rod length.

9. The apparatus of claim 2, further comprising manual control means for controlling said adjustment means of said at least one rod to adjust said rod length of said at least one rod to adjust the relative positions of said plurality of support members and switch means for selecting between a manual mode in which only said manual control means controls said adjustment means and an automatic mode in which only said automatic drive means controls said adjustment means.

10. The apparatus of claim 9, wherein said adjustment means of said at least one rod comprises a nut.

11. The apparatus of claim 2, wherein each of said plurality of support members comprises a ring having a plurality of through holes.

12. The apparatus of claim 11, wherein at least one of said plurality of support members is secured to said article by means of pins secured at said through holes.

13. The apparatus of claim 2, wherein said at least one rod comprises a graduated telescopic rod.

14. The apparatus of claim 13, wherein said at least one motor is a digital motor and at least one of said digital motors is mounted on said at least one of said graduated telescopic rods and said apparatus further comprises:

(i) a gear mount ring mounted around an adjustment nut of said at least one rod, said gear mount ring comprising on one end a detent latching loop engaged with a projection of said nut such that said gear mount ring and said nut are rotatable in concert and on its other end an internal gear ring; and (ii) a gear box connected to said digital motor and comprising an output gear comprising gear means for engagement with said internal gear ring of said gear mount ring.

15. The apparatus of claim 14, further comprising means for enabling said gear mount ring to move axially relative to said adjustment nut so as to cause said gear mount ring to disengage from said output gear while maintaining engagement between said detent latching loop and said projection of said nut, whereby when said gear mount ring is disengaged from said output gear, a manual mode is provided in which said adjustment nut can be manually rotated, and, when said gear mount ring is engaged with said output gear, an automatic mode is provided in which said adjustment nut can be rotated by said automatic drive means.

16. The apparatus of claim 2, wherein said at least one motor is a digital motor.

17. The apparatus of claim 2, wherein said controller means comprises means for providing a test pulse to said at least one motor and for checking whether said at least one motor responds properly to said pulse.

18. The apparatus of claim 17, wherein said controller means further comprises:

(i) a counter;

(ii) means for loading into said counter a predetermined count representing a total number of pulses required to be sent to said at least one motor to step the motor a required amount at each advance cycle and a total cycle count representing a number of advance cycles required for said at least one motor to achieve a desired total positioning movement;

(iii) pulse provision means for providing a control pulse to a first one of said at least one motor to advance it one increment;

(iv) first determination means for determining whether said first one of said at least one motor is turned on in response to said control pulse;

(v) motor turnoff means for turning off said first one of said at least one motor;

(vi) second determination means for determining whether said first one of said at least one motor is turned off;

(vii) decrement means for decrementing said predetermined count stored in said counter to provide a decremented count responsive to said pulse provision means advancing said first one of said at least one motor one increment; and (viii) means for checking whether the decremented count stored in said counter is greater than zero, for causing said pulse provision means, said first determination means, said motor turnoff means, said second determination means and said decrement means to operate again with respect to said first one of said at least one motor.

19. The apparatus of claim 18, wherein said means for loading further comprises means, responsive to said means for checking making a determination that said decremented count is equal to zero, for causing said predetermined count to be again loaded into said counter and said controller means further comprises means, responsive to said means for determining making a determination that said decremented count is equal to zero, for causing said pulse provision means, said second determination means and said decrement means to operate successively with respect to all other ones of said digital motors to complete an advance cycle for said motors.

20. The apparatus of claim 19, wherein said controller means further comprises:
   means for counting a number of said advance cycles through which said pulse provision means, said first determination means, said motor turnoff means, said second determination means and said decrement means have operated with respect to said motors;
   comparison means for comparing said number of said advance cycles with said total cycle count representing said number of advance cycles required to achieve said desired total positioning movement;
   delay means for causing said pulse provision means, said first determination means, said motor turnoff means, said second determination means and said decrement means to operate with respect to said motors to carry out another said advance cycle after a predetermined time delay response to a determination by said comparison means that said number of advance cycles is less than said total cycle count; and
   termination means for terminating the positioning responsive to a determination by said comparison means that said number of advance cycles is equal to said total cycle count.

21. The apparatus of claim 2, further comprising a first power supply for said at least one motor, a second power supply for said controller means, monitor means for monitoring an output level of an output from said second power supply, and switch means for switching the output of said first power supply to said controller means responsive to a determination by said monitor means that said output level of said second power supply is less than a predetermined threshold.

22. The apparatus of claim 2, wherein said article to be positioned is at least one of human or animal bone and tissue.

23. A method of controlling an orthopedic apparatus which includes a plurality of support members, at least one rod interconnecting said support members, said at least one rod comprising adjustment means for enabling the rod length to be adjusted, and a plurality of pins attached to said support members, said pins comprising means for passing through bone of a patient, said method comprising:
   controlling said adjustment means of said at least one rod to adjust said rod length of said at least one rod to adjust the relative positions of said support members by employing at least one motor corresponding to said at least one rod to incrementally adjust said adjustment means to adjust said rod length and employing a controller means for controlling and monitoring incremental adjustments of said at least one rod and to store information regarding the number of adjustments of said rod length by said at least one motor.

24. A method for positioning an article utilizing an apparatus which includes a plurality of support members, at least one adjustable length rod interconnecting said support members, said at least one rod comprising adjustment means for enabling adjustment of said rod length, and a plurality of attachment means connected to at least one of said plurality of support members for securing at least one of said plurality of support members to said article to be positioned, said method comprising:
   controlling said adjustment means for said at least one rod to adjust the length of said at least one rod to thereby adjust the relative positions of said plurality of support members by employing at least one motor corresponding to said at least one rod to increment and adjust said adjustment means to stepwise adjust said length of said at least one rod.

25. The method of claim 24, further comprising the steps of employing a controller means to provide pulses to said at least one motor to control the incremental adjustments of said at least one rod and for storing information regarding the number of stepwise adjustments of said rod length by said at least one motor.

26. The method of claim 25, further comprising sensing the amount of adjustment of said rod length of said at least one rod and providing data representing said sensed amount of adjustment to said controller means based on a comparison of information regarding the number of stepwise adjustments with said data representing said sensed amount of adjustment.

27. The method of claim 25, further comprising displaying a representation of said information regarding said number of stepwise adjustments of said rod length.

28. The method of claim 24, further comprising providing a test pulse to said at least one motor and checking whether said at least one motor responds properly to said pulse.

29. The method of claim 24, further comprising:
   (i) storing in a counter a predetermined count representing a total number of pulses required to be sent to said at least one motor to step the motor a required amount at each advance cycle and a total cycle count representing a number of advance cycles required for said at least one motor to achieve a desired total positioning movement;
   (ii) providing a control pulse to a first one of said at least one motor to advance it one increment;
   (iii) determining whether said first one of said at least one motor is turned on in response to said control pulse;
   (iv) turning off said first one of said at least one motor;
   (v) determining whether said first one of said at least one motor is turned off;
   (vi) decrementing said predetermined count stored in step (i) to provide a decremented count responsive to said first one of said at least one motor being advanced one increment; and
   (vii) checking whether the decremented count obtained in step (vi) is greater than zero, and if said decremented count is greater than zero, repeating steps (ii)–(vi) with respect to said first one of said at least one motor.

30. The method of claim 29, further comprising, responsive to a determination that said decremented count obtain in step (vi) is equal to zero, storing again in said counter said predetermined count and performing steps (i)–(vii) successively with respect to all other ones of said motors to complete an advance cycle for said motor.

31. The method of claim 30, further comprising:
   counting a number of said advance cycles carried out with respect to said motors;
   comparing said number of said advance cycles with said total cycle count representing said number of advance cycles required to achieve said desired total positioning movement;

performing steps (i)-(vii) with respect to said motors to carry out another said advance cycle after a predetermined time delay responsive to a determination that said number of advance cycles is less than said total cycle count; and terminating the positioning responsive to a determination that said number of advance cycles is equal to said total cycle count.

32. The method of claim 24, wherein said at least one motor comprises a digital motor.

* * * * *